United States Patent
Lee et al.

(10) Patent No.: US 12,187,806 B2
(45) Date of Patent: Jan. 7, 2025

(54) ANTI-CD73 ANTIBODIES AND USE THEREOF

(71) Applicant: Development Center for Biotechnology, New Taipei (TW)

(72) Inventors: Chun-Chung Lee, Taipei (TW); Yu-Hsun Lo, Taipei (TW); Chu-Bin Liao, Taipei (TW); Chen-Jei Hong, Taipei (TW); Sih-Yu Chen, Taipei (TW); Yen-Yu Wu, Taipei (TW); Szu-Liang Lai, Taipei (TW); Chih-Yung Hu, Taipei (TW); Wen-Bin Ke, Taipei (TW); Ya-Ting Juan, Taipei (TW); Kao-Jean Huang, Taipei (TW)

(73) Assignee: DEVELOPMENT CENTER FOR BIOTECHNOLOGY, New Taipei (TW)

( * ) Notice: Subject to any disclaimer, the term of this patent is extended or adjusted under 35 U.S.C. 154(b) by 0 days.

(21) Appl. No.: 17/686,666

(22) Filed: Mar. 4, 2022

(65) Prior Publication Data
US 2023/0279139 A1    Sep. 7, 2023

(51) Int. Cl.
*C07K 16/28* (2006.01)
*A61K 39/395* (2006.01)
*A61K 45/06* (2006.01)
*A61P 35/00* (2006.01)
*A61K 39/00* (2006.01)

(52) U.S. Cl.
CPC .... *C07K 16/2896* (2013.01); *A61K 39/39558* (2013.01); *A61K 45/06* (2013.01); *A61P 35/00* (2018.01); *A61K 2039/505* (2013.01); *C07K 2317/24* (2013.01); *C07K 2317/34* (2013.01); *C07K 2317/622* (2013.01); *C07K 2317/75* (2013.01); *C07K 2317/76* (2013.01); *C07K 2317/92* (2013.01)

(58) Field of Classification Search
CPC .......... C07K 16/2896; A61K 2039/505; A61K 39/39558; A61P 35/00
See application file for complete search history.

(56) References Cited

U.S. PATENT DOCUMENTS

| | | | |
|---|---|---|---|
| 9,090,697 | B2 | 7/2015 | Sim |
| 9,388,249 | B2 | 7/2016 | Sugioka et al. |
| 9,605,080 | B2 | 3/2017 | Lonberg et al. |
| 9,938,356 | B2 | 4/2018 | Hay et al. |
| 2016/0129108 | A1 | 5/2016 | Sachsenmeier et al. |
| 2018/0009899 | A1 | 1/2018 | Griffin et al. |
| 2018/0030144 | A1 | 2/2018 | Chanteux et al. |
| 2018/0125973 | A1 | 5/2018 | Sachsenmeier et al. |
| 2019/0225703 | A1 | 7/2019 | Caux et al. |
| 2020/0079877 | A1 | 3/2020 | Hay et al. |
| 2020/0399389 | A1* | 12/2020 | Wang ............... A61P 35/00 |
| 2022/0098319 | A1 | 3/2022 | Wang et al. |
| 2022/0162331 | A1 | 5/2022 | Xu et al. |

FOREIGN PATENT DOCUMENTS

| | | |
|---|---|---|
| CN | 106852149 A | 6/2017 |
| EP | 3 362 475 A1 | 8/2018 |
| TW | 201905001 A | 2/2019 |
| WO | WO 2016/131950 A1 | 8/2016 |
| WO | WO 2017/064043 A1 | 4/2017 |
| WO | WO 2017/100670 A1 | 6/2017 |
| WO | WO 2017/118613 A1 | 7/2017 |
| WO | WO 2017/152085 A1 | 9/2017 |
| WO | WO 2018/110555 A1 | 6/2018 |
| WO | WO 2018/137598 A1 | 8/2018 |
| WO | WO 2018/187512 A1 | 10/2018 |
| WO | WO 2018/215535 A1 | 11/2018 |
| WO | WO 2018/237157 A1 | 12/2018 |
| WO | WO 2018/237173 A1 | 12/2018 |
| WO | WO 2019/046815 A1 | 3/2019 |
| WO | WO 2019/224025 A2 | 11/2019 |
| WO | WO 2019/232244 A2 | 12/2019 |
| WO | WO 2020/143710 A1 | 7/2020 |
| WO | WO 2020/143836 A1 | 7/2020 |

OTHER PUBLICATIONS

Antonioli L, Yegutkin GG, Pacher P, Blandizzi C, Haskó G. Anti-CD73 in cancer immunotherapy: awakening new opportunities. Trends Cancer. Feb. 1, 2016;2(2):95-109 (Year: 2016).*
Almagro JC, Fransson J. Humanization of antibodies. Front Biosci. Jan. 1, 2008;13:1619-33. (Year: 2008).*
Kussie et al. A single engineered amino acid substitution changes antibody fine specificity.J Immunol. Jan. 1, 1994;152(1):146-52. ( Year: 1994).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding.PNAS Jan. 24, 2017 114(4)E486-E495;firstpublished Jan. 5, 2017. (Year: 2017).*
Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Jennifer A Benavides
(74) *Attorney, Agent, or Firm* — Christensen, Fonder, Dardi & Herbert PLLC

(57) ABSTRACT

The present invention relates to a novel antibody, an antigen-binding fragment thereof and the uses of the antibody and fragment, wherein the antibody and the fragment comprise specific complementarity-determining regions (CDRs) and/or specifically bind to human CD73 at specific epitopes.

33 Claims, 18 Drawing Sheets
(5 of 18 Drawing Sheet(s) Filed in Color)
Specification includes a Sequence Listing.

(56) References Cited

OTHER PUBLICATIONS

Rudikoff S et al. Single amino acid substitution altering antigen-binding specificity. Proc Natl Acad Sci U S A. Mar. 1982;79(6):1979-83. (Year: 1982).*

Murphy C, Stack E, Krivelo S, Breheny M, Ma H, O'Kennedy R. Enhancing recombinant antibody performance by optimally engineering its format. J Immunol Methods. Dec. 2018;463:127-133. (Year: 2018).*

Coustan-Smith, Elaine, et al., "New markers for minimal residual disease detection in acute lymphoblastic leukemia," Blood, vol. 117, No. 23, pp. 6267-6276 (Jun. 9, 2011).

Wang, H., et al., "NT5E (CD73) is epigenetically regulated in malignant melanoma and associated with metastatic site specificity," British Journal of Cancer, vol. 106, pp. 1446-1452 (2012).

Wang, X., et al., "Tumor CD73/A2aR adenosine immunosuppressive axis and tumor-infiltrating lymphocytes in diffuse large B-cell lymphoma: correlations with clinicopathological characteristics and clinical outcome," Int. J. Cancer, vol. 145, pp. 1414-1422 (2019).

Wettstein, Marian S., et al., "CD73 Predicts Favorable Prognosis in Patients with Nonmuscle-Invasive Urothelial Bladder Cancer," Disease Markers, vol. 2015, Article ID 785461, 8 pages (2015).

Liu, Nan, et al., "CD73 as a Novel Prognostic Biomarker for Human Colorectal Cancer," J. Surg. Oncol., vol. 106(7), pp. 918-919 (2012).

Loi, Sherene, et al., "CD73 promotes anthracycline resistance and poor prognosis in triple negative breast cancer," PNAS, vol. 110, No. 27, pp. 11091-11096 (Jul. 2, 2013).

Lu, Xiao-Xia, et al., Expression and clinical significance of CD73 and hypoxia-inducible factor-1a in gastric carcinoma, World J. Gastroenterol., vol. 19 (12), pp. 1912-1918 (Mar. 28, 2013).

Serra, Sara, et al., "CD73-generated extracellular adenosine in chronic lymphocytic leukemia creates local conditions counteracting drug-induced cell death," Blood, vol. 118, No. 23, pp. 6141-6152 (Dec. 1, 2011).

Jiang, Tao, et al., "Comprehensive evaluation of NT5E/CD73 expression and its prognostic significance in distinct types of cancers," BMC Cancer, vol. 18:267, 10 pages (2018).

Turcotte, Martin, et al., "CD73 Is Associated with Poor Prognosis in High- Grade Serous Ovarian Cancer," Cancer Res, vol. 75(21), pp. 4494-4503 (Nov. 1, 2015).

Wu, Xian-Rui, et al., "High Expression of CD73 as a Poor Prognostic Biomarker in Human Colorectal Cancer," J. Surg. Oncol., vol. 106(2), pp. 130-137 (2012).

Xiong, Li, et al., "NT5E and FcGBP as key regulators of TGF-1-induced epithelial-mesenchymal transition (EMT) are associated with tumor progression and survival of patients with gallbladder cancer," Cell Tissue Res., vol. 355, pp. 365-374 (2014).

Xu, Shuo, et al., Synergy between the ectoenzymes CD39 and CD73 contributes to adenosinergic immunosuppression in human malignant gliomas, Neuro-Oncology, vol. 15(9), pp. 1160-1172 (2013).

Yang, Qing, et al., "Overexpression of CD73 in Prostate Cancer is Associated with Lymph Node Metastasis," Pathol. Oncol. Res., vol. 19, pp. 811-814 (2013).

Zhang, Bin, et al., "The expression and clinical significance of CD73 molecule in human rectal adenocarcinoma," Tumor Biol., vol. 36(7), pp. 5459-5466 (2015).

Zhi, Xiuling, et al., "RNAi-mediated CD73 suppression induced apoptosis and cell-cycle arrest in human breast cancer cells," Cancer Sci., vol. 101, No. 12, pp. 2561-2569 (Dec. 2010).

Ren, Zhen-Hu, et al., "CD73 is associated with poor prognosis in HNSCC," Oncotarget, vol. 7, No. 38, pp. 61690-61702 (2016).

Zhi, Xiuling, et al., "RNA interference of ecto-5'-nucleotidase (CD73) inhibits human breast cancer cell growth and invasion," Clin. Exp. Metastasis, vol. 24, pp. 439-448 (2007).

Geoghegan, James C., et al., "Inhibition of CD73 AMP hydrolysis by a therapeutic antibody with a dual, non-competitive mechanism of action," MABS, vol. 8, No. 3, pp. 454-467 (2016).

Hay, Carl M., et al., "Targeting CD73 in the tumor microenvironment with MEDI9447," Oncoimmunology, vol. 5, No. 8, 10 pages (2016).

Allard, Bertrand, et al., "Targeting CD73 Enhances the Antitumor Activity of Anti-PD-1 and Anti-CTLA-4 mAbs," Clin. Cancer Res., vol. 19(20) pp. 5626-5635 (Oct. 15, 2013).

Young, Arabella, et al., "Co-inhibition of CD73 and A2AR Adenosine Signaling Improves Anti-tumor Immune Responses," Cancer Cell, vol. 30, pp. 391-403 (Sep. 12, 2016).

Qiao, Zheng, et al., "A Novel Specific Anti-CD73 Antibody Inhibits Triple- Negative Breast Cancer Cell Motility by Regulating Autophagy," Int. J. Mol. Sci., vol. 20, 1057, 15 pages (2019).

Stagg, John, et al., "Anti-C73 antibody therapy inhibits breast tumor growth and metastasis," PNAS, vol. 107, No. 4, pp. 1547-1552 (Jan. 26, 2010).

Tu, Eric, et al., "Anti-PD-LI and anti-CD73 combination therapy promotes T cell response to EGFR-mutated NSCLC," JCI Insight., vol. 7(3), 14 pages (Feb. 8, 2022).

Allard, Bertrand, et al., "Anti-CD73 therapy impairs tumor angiogenesis," Int. J. Cancer, vol. 134, pp. 1466-1473 (2014).

Terp, Mikkel G., et al., "Anti-Human CD73 Monoclonal Antibody Inhibits Metastasis Formation in Human Breast Cancer by Inducing Clustering and Internalization of CD73 Expressed on the Surface of Cancer Cells," J. Immunol., vol. 191, pp. 4165-4173 (2013).

Vijayan, Dipti, et al., "Selective activation of anti-CD73 mechanisms in control of primary tumors and metastases," Oncoimmunology, vol. 6, No. 5, 11 pages (2017).

Antonioli, Luca, et al., "Anti-CD73 in cancer immunotherapy: awakening new opportunities," Trends Cancer, vol. 2(2), pp. 95-109 (Feb. 1, 2016).

Deng, Wei-Wei, et al., "Specific blockade CD73 alters the "exhausted" phenotype of T cells in head and neck squamous cell carcinoma," Int. J. Cancer, vol. 143, pp. 1494-1504 (2018).

Stagg, John, et al., "CD73-Deficient Mice Have Increased Antitumor Immunity and Are Resistant to Experimental Metastasis," Cancer Res., vol. 71(8), pp. 2892-2900 (Apr. 15, 2011).

Hugo, Ferdinand, et al., "In Vitro Effect of Extracellular AMP on MCF-7 Breast Cancer Cells: Inhibition of Glycolysis and Cell Proliferation," Journal of Cellular Physiology, vol. 153, pp. 539-549 (1992).

Mittal, Deepak, et al., "Antimetastatic Effects of Blocking PD-1 and the Adenosine A2A Receptor," Cancer Res, 74(14):3652-3658 (Jul. 15, 2014).

Reinhardt, Julia, et al., "MAPK Signaling and Inflammation Link Melanoma Phenotype Switching to Induction of CD73 During Immunotherapy," Cancer Res, 77(17):4697-4709 (Sep. 1, 2017).

Goswami, Sangeeta, et al., "Immune profiling of human tumors identifies CD73 as a combinatorial target in glioblastoma," Nat Med., 26(1):39-46 (Jan. 2020).

Iannone, Raffaella, et al., "Adenosine limits the therapeutic effectiveness of anti-CTLA4 mAb in a mouse melanoma model," Am J Cancer Res 4(2):172-181 (2014).

Neo, Shi Yong, et al., "CD73 immune checkpoint defines regulatory NK cells within the tumor microenvironment," J Clin Invest., 130(3):1185-1198. Doi.org/ 10.1172/JCI128895. PMID: 31770109; PMCID: PMC7269592 (Mar. 2, 2020).

Kobie, James J., et al., "T Regulatory and Primed Uncommitted CD4 t Cells Express CD73, Which Suppresses Effector CD4 T Cells by Converting 5'-Adenosine Monophosphate to Adenosine," J Immunol, 177(10):6780-6786 (2006).

Wang, Long, et al., "CD73 has distinct roles in nonhematopoietic and hematopoietic cells to promote tumor growth in mice," J Clin Invest 121(6):2371-2382 (Jun. 2011).

Capone, Mariaelena, et al., "Frequency of circulating CD8+ CD73+T cells is associated with survival in nivolumab-treated melanoma patients," J Transl Med 18(1):121 (2020).

Chambers, Andrea M., et al., "Immunometabolic Dysfunction of Natural Killer Cells Mediated by the Hypoxia-CD73 Axis in Solid Tumors," Frontiers in Molecular Biosciences, 6, Article 60: 1-13 (Jul. 24, 2019).

Li, Lifeng, et al., "Metformin-induced reduction of CD39 and CD73 blocks myeloid-derived suppressor cell activity in patients with ovarian cancer," Cancer Res 78(7):1779-1791 (Apr. 1, 2018).

(56) References Cited

OTHER PUBLICATIONS

Li, Jieyao, et al., "CD39/CD73 upregulation on myeloid-derived suppressor cells via TGF-β-mTOR-HIF-1 signaling in patients with non-small cell lung cancer," *Oncoimmunology* 6(6):e1320011 (2017).

Yegutkin, Gennady G., et al., "Altered purinergic signaling in CD73-deficient mice inhibits tumor progression," *Eur J Immunol* 41(5):1231-1241 (2011).

Zanin, Rafael Fernandes, et al., "Differential Macrophage Activation Alters the Expression Profile of NDPDase and Ecto-5'-Nucleotidase," *PLoS One,* 7(2):e31205 (Feb. 2012).

Forte, Giovanni, et al., "Inhibition of CD73 improves B cell-mediated anti-tumor immunity in a mouse model of melanoma," *J Immunol,* 189(5):2226-2233 (Sep. 1, 2012).

Hesse, Julia, et al., Profound inhibition of CD73-dependent formation of anti-inflammatory adenosine in B cells of SLE patients,: *EBioMedicine,* 73: 103616 (2021).

Rust, Steven, et al., "Combining phenotypic and proteomic approaches to identify membrane targets in a 'triple negative' breast cancer cell type," Molecular Cancer, vol. 12, 11 pages (2013).

\* cited by examiner

FIG. 9

| Ab | mutation | Seq ID No | Binding Affinity (K$_D$) to Mouse CD73 D296E-K297R ($10^{-10}$M) |
|---|---|---|---|
| 10-H5 | Wild type | 2, 3 | 0.98 |
| 109A03 | HCDR3 position 1 Phe to Leu | 29, 3 | 0.57 |
| 110A06 | HCDR2 position 1 Gln to Ser | 30, 3 | 0.80 |
| 110B03 | LCDR3 position 8 Leu to Met | 2, 39 | 0.36 |
| 111B03 | LCDR3 position 8 Leu to Gly | 2, 40 | 0.48 |
| 111D04 | HCDR2 position 1 Gln to Arg; HCDR3 position 1 Phe to Tyr | 31, 3 | 1.38 |
| 112A05 | HCDR3 position 1 Phe to Ile | 32, 3 | 0.71 |
| 112B02 | LCDR3 position 8 Leu to His | 2, 41 | 2.07 |
| 113D04 | LCDR3 position 8 Leu to Arg | 2, 42 | 0.65 |
| 114B07 | HCDR2 position 1 Gln to Thr | 33, 12 | 1.38 |
| 114C01 | HCDR2 position 1 Gln to His; HCDR3 position 1 Phe to Tyr | 34, 12 | 0.59 |
| 114C12 | HCDR1 position 8 Trp to Thr; HCDR2 position 1 Gln to Arg | 35, 12 | 0.59 |
| 114D07 | HCDR2 position 1 Gln to Arg | 36, 12 | 3.33 |
| 114E08 | LCDR3 position 8 Leu to Gln | 11, 43 | 0.69 |
| 114G05 | HCDR2 position 1 Gln to His | 37, 12 | 1.30 |
| 116C07 | LCDR3 position 8 Leu to Ile | 11, 44 | 1.40 |
| 116G02 | HCDR2 position 1 Gln to Arg; HCDR3 position 1 Phe to Leu | 38, 12 | 0.84 |

ANTI-CD73 ANTIBODIES AND USE THEREOF

FIELD OF THE INVENTION

The present invention relates to novel antibodies, antigen-binding fragments of the antibodies and uses of the antibodies and fragments, wherein the antibodies and the fragments comprise specific complementarity-determining regions (CDRs) and/or specifically bind to human CD73 at specific epitopes.

BACKGROUND OF THE INVENTION

The immunosuppressive effects in the tumor microenvironment are closely related to the progression of tumor growth. Tumor cells can change the microenvironment to escape immune surveillance. In recent research, several tumor-induced immune escape mechanisms have been found, wherein the co-inhibitory receptors (also called immune checkpoints, such as CTLA-4, PD-1) expressed on the T-cell surface have been taken as the targets of immunotherapy and successfully developed as immune checkpoint-inhibiting drugs.

During inflammation, adenosine triphosphate (ATP) is released from inflammatory cells, and the extracellular ATP attracts dendritic cells, macrophages or neutrophils via binding to the purinergic receptors (e.g., P2X receptor and P2Y receptor) expressed on the surface of these immune cells and causing immune responses. Moreover, extracellular ATP can also act as a source of immunosuppressant adenosine via CD39 and CD73 mediated hydrolysis. When inflammation is over, the membrane protein CD39 will convert ATP into adenosine diphosphate (ADP) or adenosine monophosphate (AMP) and the membrane protein CD73 will convert AMP into adenosine. Adenosine can inhibit the immune responses by binding to the receptors of immune cells (especially A2A and A2B receptors) and promoting the synthesis of cAMP that protect tissue from over inflammation. Beyond the role in regulation of immune response, the immunosuppressive effect of adenosine has also been recently reported as a critical factor that promote tumor growth. In the tumor microenvironment, the release of ATP and expression of CD39 and CD73 are increased due to hypoxia-induced tumor cells necrosis, and this causes an accumulation of adenosine. Furthermore, the expressions of A2A receptor and A2B receptor on immune cells are also increased due to the anoxic environment around the tumor. It has been proved that CD73 can promote the growth and angiogenesis of tumors, and the adenosine-induced immune-suppression, which are different from the other known mechanisms (e.g., suppressing immune response through immune-receptor tyrosine-based inhibition motif (ITIM)). The high expressions of CD73 and adenosine both are highly correlated with the progression and metastasis of tumors. Some inhibitors of adenosine signaling by targeting CD73 or adenosine A2A receptor, are expected to have a synergistic effect when used in combination with other immunotherapy drugs for cancer therapy. Therefore, for the purpose of cancer therapy, the drugs or methods targeting CD73 are under aggressive development for inhibiting the production of adenosine and/or the adenosine-induced immune-suppression.

Several kinds of anti-CD73 antibodies are undergoing phase 1 or phase 2 clinical trials, used alone or in combination with other drugs such as anti-PD-1, anti-PDL1, anti-CTLA4, EGFR inhibitor, and A2AR inhibitor (e.g., Ipilimumab and Nivolumab). For instance, Oleclumab (MEDI9447), a human anti-CD73 antibody, is currently being evaluated in a clinical trial. Nevertheless, there is still a necessity and urgency for developing novel anti-CD73 antibodies that can provide a better inhibitory effect on CD73.

SUMMARY OF THE INVENTION

Inventors of the present invention discovered novel antibodies and the antigen-binding fragments thereof. The novel antibodies and antigen-binding fragments comprise specific complementarity-determining regions (CDRs) and can specifically bind to human CD73 at specific epitopes (e.g., the glutamic acid residue at position 296 and the arginine residue at position 297), and thus can inhibit CD73 activity and inhibit AMP consumption. Furthermore, compared to the positive control (i.e., Oleclumab), the antibodies and antigen-binding fragments of the present invention have a better and more long-term effective duration of inhibiting AMP consumption, and a better effect on activating immune cells and inhibiting tumor growth.

Therefore, an objective of the present invention is to provide an antibody or an antigen-binding fragment thereof, comprising: (i) a heavy chain variable domain comprising a HCDR1 region, a HCDR2 region, and a HCDR3 region, wherein the HCDR1 region comprises an amino acid sequence of SEQ ID NO: 4 with at most one variation, the HCDR2 region comprises an amino acid sequence of SEQ ID NO: 5 with at most one variation, and the HCDR3 region comprises an amino acid sequence of SEQ ID NO: 6 with at most one variation; and (ii) a light chain variable domain comprising a LCDR1 region, a LCDR2 region, and a LCDR3 region, wherein the LCDR1 region comprises an amino acid sequence of SEQ ID NO: 7 with at most one variation, the LCDR2 region comprises an amino acid sequence of SEQ ID NO: 8 with at most one variation, and the LCDR3 region comprises an amino acid sequence of SEQ ID NO: 9 with at most one variation.

Preferably, in the antibody or antigen-binding fragment thereof in accordance with the present invention as described above, the HCDR1 region comprises an amino acid sequence of SEQ ID NO: 4 with at most one variation, the HCDR2 region comprises an amino acid sequence of SEQ ID NO: 5 with at most one variation, and the HCDR3 region comprises an amino acid sequence of SEQ ID NO: 6 with at most one variation; and the LCDR1 region comprises an amino acid sequence of SEQ ID NO: 7, the LCDR2 region comprises an amino acid sequence of SEQ ID NO: 8, and the LCDR3 region comprises an amino acid sequence of SEQ ID NO: 9 with at most one variation.

In certain embodiments of the antibody or antigen-binding fragment thereof in accordance with the present invention as described above, the HCDR1 region comprises an amino acid sequence of SEQ ID NO: 4 with variation at position 8; the HCDR2 region comprises an amino acid sequence of SEQ ID NO: 5 with variation at position 1; the HCDR3 region comprises an amino acid sequence of SEQ ID NO: 6 with variation at position 1; the LCDR1 region comprises an amino acid sequence of SEQ ID NO: 7, the LCDR2 region comprises an amino acid sequence of SEQ ID NO: 8; and the LCDR3 region comprises an amino acid sequence of SEQ ID NO: 9 with variation at position 8. Preferably, the HCDR1 region comprises an amino acid sequence of SEQ ID NO: 4, wherein the tryptophan residue at position 8 is substituted by threonine; the HCDR2 region comprises an amino acid sequence of SEQ ID NO: 5, wherein the glutamine residue at position 1 is substituted by serine, arginine, threonine or histidine, the HCDR3 region comprises an amino acid sequence of SEQ ID NO: 6, wherein the phenylalanine residue at position 1 is substituted by leucine, tyrosine or isoleucine; and the LCDR3 region comprises an amino acid sequence of SEQ ID NO: 9, wherein the leucine residue at position 8 is substituted by methionine, glycine, histidine, arginine, glutamine or isoleucine.

In certain embodiments of the antibody or antigen-binding fragment thereof in accordance with the present invention as described above, the HCDR1 region comprises an amino acid sequence selected from the group consisting of SEQ ID NO: 4 and SEQ ID NO: 15; the HCDR2 region comprises an amino acid sequence selected from the group consisting of SEQ ID NO: 5, SEQ ID NO: 16 to SEQ ID NO: 19; and the HCDR3 region comprises an amino acid sequence selected from the group consisting of SEQ ID NO:6 (FAD); SEQ ID NO: 20 (LAD); SEQ ID NO: 21 (YAD) and SEQ ID NO: 22 (IAD). In certain embodiments of the antibody or antigen-binding fragment thereof in accordance with the present invention as described above, the LCDR1 region comprises an amino acid sequence of SEQ ID NO: 7; the LCDR2 region comprises an amino acid sequence of SEQ ID NO: 8; and the LCDR3 region comprises an amino acid sequence selected from the group consisting of SEQ ID NO: 9, SEQ ID NO: 23 to SEQ ID NO: 28.

In certain embodiments of the antibody or antigen-binding fragment thereof in accordance with the present invention as described above, the heavy chain variable domain comprises an amino acid sequence selected from the group consisting of: (i) an amino acid sequence having at least 95% identity to SEQ ID NO: 2 (i.e., 10H5 chimeric Heavy chain), (ii) an amino acid sequence having at least 95% identity to SEQ ID NO: 10 (i.e., 10H5 humanized Heavy chain HuB9), and (iii) an amino acid sequence having at least 95% identity to SEQ ID NO: 11 (i.e., 10H5 humanized Heavy chain HuB10). More preferably, the heavy chain variable domain comprises an amino acid sequence selected from the group consisting of SEQ ID NO: 2, SEQ ID NO: 10, SEQ ID NO: 11 and SEQ ID NO: 29 to SEQ ID NO: 38.

In certain embodiments of the antibody or antigen-binding fragment thereof in accordance with the present invention as described above, the light chain variable domain comprises an amino acid sequence selected from the group consisting of: (i) an amino acid sequence having at least 95% identity to SEQ ID NO: 3 (i.e., 10H5 chimeric Light chain), (ii) an amino acid sequence having at least 95% identity to SEQ ID NO: 12 (i.e., 10H5 humanized Light chain HdB6), and (iii) an amino acid sequence having at least 95% identity to SEQ ID NO: 13 (i.e., 10H5 humanized Light chain HdB7). More preferably, the light chain variable domain comprises an amino acid sequence selected from the group consisting of SEQ ID NO: 3, SEQ ID NO: 12, SEQ ID NO: 13 and SEQ ID NO: 39 to SEQ ID NO: 44.

In certain embodiments of the present invention, the antibody or antigen-binding fragment thereof as described above further comprises one or more of (1) a linker peptide between the heavy chain variable domain and the light chain variable domain, (2) a heavy chain constant region, (3) a light chain constant region, and (4) an Fc region.

Preferably, the antibody or antigen-binding fragment thereof in accordance with the present invention as described above is a single chain antibody fragment, a bispecific antibody, a single-domain antibody, a nanobody, a chimeric antibody, or a partially or fully humanized antibody.

More preferably, the antibody or antigen-binding fragment thereof further links with a drug conjugate to form an antibody-drug conjugate (ADC), or further links with a second antibody or a second antigen binding fragment to form a bispecific antibody.

In various embodiments of the present invention, the heavy chain constant region or fragment thereof is an IgG constant region, including for example an IgG1 constant region, an IgG2 constant region, an IgG3 constant region or an IgG4 constant region. In one embodiment, the antibody or antigen-binding fragment thereof further comprises a fragment derived from IgG4.

In various embodiments of any aspect delineated herein, the IgG constant region has one or more amino acid substitutions relative to a wild-type IgG constant region where the modified IgG has an increased half-life compared to the half-life of an IgG having the wild-type IgG constant region.

In various embodiments of any aspect delineated herein, the IgG constant region has one or more amino acid substitutions of amino acid residues at positions 251-257, 285-290, 308-314, 385-389, and 428-436, where the numbering is according to the EU index as set forth in Kabat.

In various embodiments of any aspect delineated herein, the antigen-binding fragment is Fv, Fab, F(ab')2, Fab', dsFv, scFv, or sc(Fv)2.

In certain embodiments of the present invention, the antibody or antigen-binding fragment thereof as described above further comprises a fragment derived from IgG, IgM, IgA, IgE or IgD.

In certain embodiments of the present invention, the antibody or antigen-binding fragment thereof as described above specifically binds to CD73. Preferably, the antibody or antigen-binding fragment thereof specifically binds to CD73 comprising an amino acid sequence of SEQ ID NO: 14 (i.e., human CD73 269-304). More preferably, the antibody or antigen-binding fragment thereof specifically binds to CD73 comprising an amino acid sequence of SEQ ID NO: 1 (i.e., human CD73).

In certain embodiments of the present invention, the antibody or antigen-binding fragment thereof as described above binds to the CD73 on at least one of the glutamic acid residue at position 296 and the arginine residue at position 297. Preferably, the antibody or antigen-binding fragment thereof binds to the CD73 on both the glutamic acid residue at position 296 and the arginine residue at position 297.

Another objective of the present invention is to provide an antibody or an antigen-binding fragment thereof, wherein the antibody or antigen-binding fragment thereof specifically binds to human CD73 on at least one of the glutamic acid residue at position 296 and the arginine residue at position 297. Preferably, the antibody or an antigen-binding fragment thereof binds to human CD73 on both the glutamic acid residue at position 296 and the arginine residue at position 297.

Preferably, in the antibody or an antigen-binding fragment thereof in accordance with the present invention that specifically binds to human CD73 on at least one of the glutamic acid residue at position 296 and the arginine residue at position 297, the CD73 comprises an amino acid sequence of SEQ ID NO: 14 (i.e., human CD73 269-304). More preferably, the CD73 comprises an amino acid sequence of SEQ ID NO: 1 (i.e., human CD73).

Preferably, the antibody or antigen-binding fragment thereof in accordance with the present invention that specifically binds to human CD73 on at least one of the glutamic acid residue at position 296 and the arginine residue at position 297 is a single chain antibody fragment, a bispecific antibody, a single-domain antibody, a nanobody, a chimeric antibody, or a partially or fully humanized antibody. More preferably, the antibody or antigen-binding fragment thereof that specifically binds to human CD73 on at least one of the glutamic acid residue at position 296 and the arginine residue at position 297 further links with a drug conjugate to form an antibody-drug conjugate (ADC), or further links with a second antibody or a second antigen binding fragment to form a bispecific antibody.

In certain embodiments of the antibody or an antigen-binding fragment thereof in accordance with the present invention that specifically binds to human CD73 on at least one of the glutamic acid residue at position 296 and the arginine residue at position 297, the antibody or antigen-binding fragment thereof further comprises a fragment derived from IgG1, IgG2, IgG3 or IgG4. In one embodiment of the antibody or an antigen-binding fragment thereof that specifically binds to human CD73 on at least one of the glutamic acid residue at position 296 and the arginine residue at position 297, the antibody or antigen-binding fragment thereof further comprises a fragment derived from IgG4.

Still another objective of the present invention is to provide a nucleic acid molecule encoding the antibody or antigen-binding fragment thereof as described above.

Yet another objective of the present invention is to provide a vector comprising the nucleic acid molecule as described above.

Yet another objective of the present invention is to provide a recombinant host cell comprising a nucleic acid molecule and/or a vector as described above.

Yet another objective of the present invention is to provide a pharmaceutical composition comprising (i) an antibody or antigen-binding fragment thereof as described above, a nucleic acid molecule encoding the aforesaid antibody or antigen-binding fragment thereof, a vector comprising the aforesaid nucleic acid molecule, a recombinant host cell comprising the aforesaid nucleic acid molecule, or a recombinant host cell comprising the aforesaid vector, and (ii) a pharmaceutically acceptable carrier. In certain embodiments of the present invention, the pharmaceutical composition is used for inhibiting CD73. In certain embodiments of the present invention, the pharmaceutical composition further comprises one or more other immunotherapy agents.

Yet another objective of the present invention is to provide a pharmaceutical composition for use in inhibiting CD73 in a subject in need thereof, wherein the pharmaceutical composition comprises (i) an antibody or antigen-binding fragment thereof as described above, a nucleic acid molecule encoding the aforesaid antibody or antigen-binding fragment thereof, a vector comprising the aforesaid nucleic acid molecule, a recombinant host cell comprising the aforesaid nucleic acid molecule, or a recombinant host cell comprising the aforesaid vector, and (ii) a pharmaceutically acceptable carrier. In certain embodiments of the pharmaceutical composition for use in inhibiting CD73 of the present invention, the pharmaceutical composition is administered in combination with one or more other immunotherapy agents.

Preferably, the other immunotherapy agent used in the present invention is PD-1 antagonist, PD-L1 antagonist or CTLA-4 antagonist.

Preferably, the pharmaceutical composition in accordance with the present invention is used for activating T-cells, activating B-cells, activating NK cells, and/or inhibiting cancer cells.

Preferably, the pharmaceutical composition in accordance with the present invention is used for treating, ameliorating and/or preventing cancer. More preferably, the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma and lymphoma.

Yet another objective of the present invention is to provide a method of inhibiting CD73, comprising administering a subject in need thereof an effective amount of a pharmaceutical composition as described above. Preferably, the method in accordance with the present invention further comprises administering one or more other immunotherapy agents to the subject in need thereof. More preferably, the other immunotherapy agent is PD-1 antagonist, PD-L1 antagonist or CTLA-4 antagonist.

Preferably, the method in accordance with the present invention is for activating T-cells, activating B-cells, activating NK cells and/or inhibiting cancer cells.

Preferably, the method in accordance with the present invention is for treating, ameliorating and/or preventing cancer. More preferably, the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma, and lymphoma.

Yet another objective of the present invention is to provide use of the antibody or antigen-binding fragment thereof as described above in the manufacture of a medicament, wherein the medicament is for inhibiting CD73. Preferably, the medicament is used in combination with one or more other immunotherapy agents. More preferably, the other immunotherapy agent is PD-1 antagonist, PD-L1 antagonist, or CTLA-4 antagonist.

Preferably, the medicament is used for activating T-cells, activating B-cells, activating NK cells and/or inhibiting cancer cells.

Preferably, the medicament is used for treating, ameliorating, and/or preventing cancer. More preferably, the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma, and lymphoma.

Yet another objective of the present invention is to provide use of the antibody or antigen-binding fragment thereof as described above for inhibiting CD73. Preferably, the antibody or antigen-binding fragment thereof is used in combination with one or more other immunotherapy agents. More preferably, the other immunotherapy agent is PD-1 antagonist, PD-L1 antagonist, or CTLA-4 antagonist.

Preferably, the antibody or antigen-binding fragment thereof is used for activating T-cells, activating B-cells, activating NK cells and/or inhibiting cancer cells.

Preferably, the antibody or antigen-binding fragment thereof is used for treating, ameliorating and/or preventing cancer. More preferably, the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma and lymphoma.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

FIG. 2B: Calu-1 cells).

FIG. 4B: Calu-1 cells).

FIG. 9 shows the design of domain swapping of mouse CD73 protein for identifying the epitopes of the antibodies of the present invention.

FIG. 16 shows the mutation position in the CDR sequences and the binding affinity ($K_D$) to the mouse CD73 D296E-K297R of the 16 antibodies, which were selected from the phage display library constructed according to 3D modeling simulation.

DESCRIPTION OF THE PREFERRED EMBODIMENTS

Figure 1A:
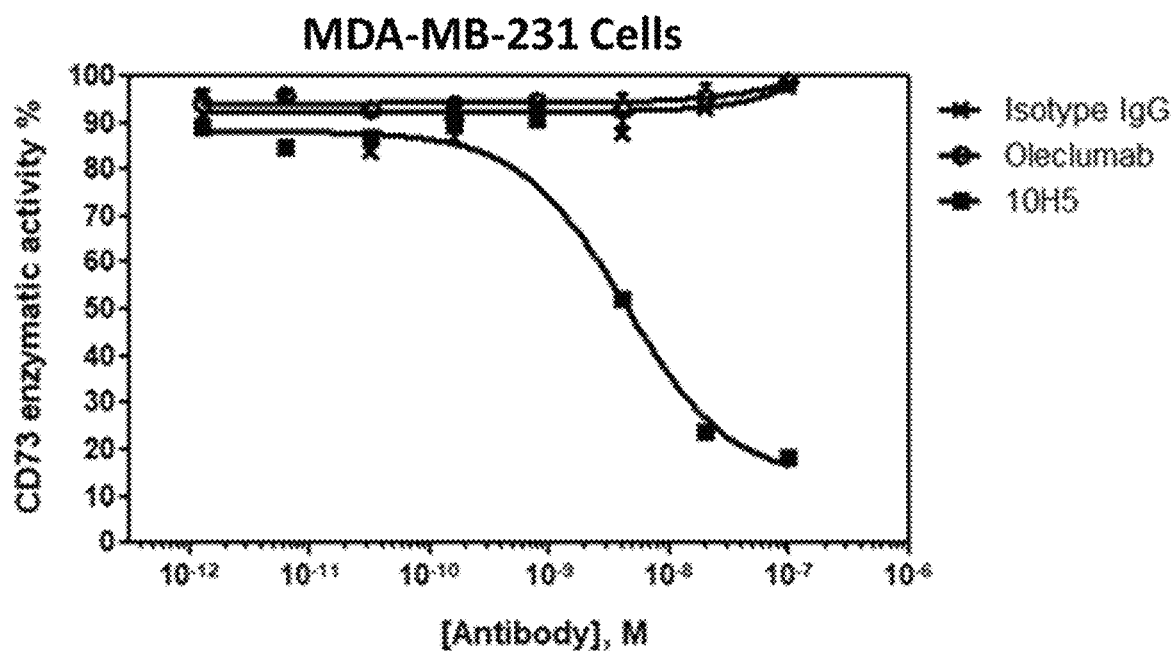
FIG. 1A indicates that the antibody of present invention, 10H5, has a superior effect on inhibiting CD73 activity than reference antibody, Oleclumab, in MDA-MB-231 triple negative breast cancer (TNBC) cells.

The following paragraphs will describe some of the embodiments of the present invention in detail. However, without departing from the spirit of the present invention, the present invention may be embodied in various embodiments and should not be limited to the embodiments described in the specification or defined in the appended claims.

Unless otherwise indicated herein, the expression "a," "an," "the," or the like recited in the specification of the present invention (especially in the claims) are intended to include both the singular and plural forms; the term "subject" recited herein refers to human or non-human mammalian (e.g., dog, cat).

The term "CD73" recited herein refers to primates CD73, such as human CD73. Human CD73 comprises an amino acid sequence of SEQ ID NO: 1, and the amino acid sequence of human CD73 at positions 269-304 is SEQ ID NO: 14.

It has been known that CD73 closely relates to the progression and prognosis of many types of cancers. The relationships between CD73 and cancers such as breast cancer (e.g., triple-negative breast cancer and invasive lobular breast cancer), gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer (e.g., oral cavity squamous cell carcinoma), lung cancer (e.g., non-small cell lung cancer, lung large cell cancer, and lung adenocarcinoma), colon adenocarcinoma, melanoma, and lymphoma can be seen in the publications listed below:

| Cancer | Publication |
| --- | --- |
| Breast cancer | Loi S, Pommey S, Haibe-Kains B, et al. CD73 promotes anthracycline resistance and poor prognosis in triple negative breast cancer. *Proc Nat Acad Sci*. 2013; 110(27): 11091-11096.<br>Tao Jiang et al. Comprehensive evaluation of NT5E/CD73 expression and its prognostic significance in distinct types of cancers. *BMC Cancer*. (2018) 18: 267. |
| Gastric cancer | Lu -X-X, Chen Y-T, Feng B, et al. Expression and clinical significance of CD73 and hypoxia-inducible factor-1α in gastric carcinoma. *World J Gastroenterol*. 2013; 19(12): 1912.<br>Tao Jiang et al. Comprehensive evaluation of NT5E/CD73 expression and its prognostic significance in distinct types of cancers. *BMC Cancer*. (2018) 18: 267. |
| Colorectal cancer | Wu XR, He XS, Chen YF, et al. High expression of CD73 as a poor prognostic biomarker in human colorectal cancer. *J Surg Oncol*. 2012; 106(2): 130-137.<br>Liu N, Fang XD, Vadis Q. CD73 as a novel prognostic biomarker for human colorectal cancer. *J Surg Oncol*. 2012; 106 (7): 918-919. |
| Gallbladder cancer patients | Xiong L, Wen Y, Miao X, et al. NT5E and FcGBP as key regulators of TGF-1-induced epithelial-mesenchymal transition (EMT) are associated with tumor progression and survival of patients with gallbladder cancer. *Cell Tissue Res*. 2014; 355(2): 365-374. |
| Prostate cancer | Yang Q, Du J, Zu L. Overexpression of CD73 in prostate cancer is associated with lymph node metastasis. *Pathol Oncol Res*. 2013 Oct; 19(4): 811-814. PubMed PMID: 23653114; eng.<br>Tao Jiang et al. Comprehensive evaluation of NT5E/CD73 expression and its prognostic significance in distinct types of cancers. *BMC Cancer*. (2018) 18: 267. |
| Ovarian carcinoma | Turcotte M, Spring K, Pommey S et al. CD73 is associated with poor prognosis in high-grade 784 serous ovarian cancer. *Cancer Res*. doi: 10.1158/0008-5472. CAN-14-3569 (2015).<br>Tao Jiang et al. Comprehensive evaluation of NT5E/CD73 expression and its prognostic significance in distinct types of cancers. *BMC Cancer* (2018) 18: 267. |
| Chronic lymphocytic leukemia | Serra S, Horenstein AL, Vaisitti T, et al. CD73-generated extracellular adenosine in chronic lymphocytic leukemia creates local conditions counteracting drug-induced cell death. *Blood*. 2011; 118 (23): 6141-6152. |
| Acute lymphocytic leukemia | Coustan-Smith E, Song G, Clark C et al. New markers for minimal residual disease detection in 866 acute lymphoblastic leukemia. *Blood*. 117(23), 6267-6276 (2011). |
| Bladder cancer | Wettstein MS, Buser L, Hermanns T et al. CD73 predicts favorable prognosis in patients with 1080 nonmuscle-invasive urothelial bladder cancer. *Disease Marker*. 2015(1), 1-8 (2015) |
| Brain tumor | Xu S, Shao QQ, Sun JT et al. Synergy between the ectoenzymes CD39 and CD73 contributes to 882 adenosinergic immunosuppression in human malignant gliomas. *Neuro Oncol*. 15(9), 1160-1172 883 (2013). |
| Kidney carcinoma | Wettstein MS, Buser L, Hermanns T et al. CD73 predicts favorable prognosis in patients with 1080 nonmuscle-invasive urothelial bladder cancer. *Disease Marker*. 2015(1), 1-8 (2015) |
| Head and neck squamous cell carcinoma | CD73 is associated with poor prognosis in HNSCC *Oncotarget*. 2016 Sep 20; 7(38): 61690-61702. |
| Glioblastoma | Tao Jiang et al. Comprehensive evaluation of NT5E/CD73 expression and its prognostic significance in distinct types of cancers. *BMC Cancer*. (2018) 18: 267. |
| Esophageal cancer | Tao Jiang et al. Comprehensive evaluation of NT5E/CD73 expression and its prognostic significance in distinct types of cancers. *BMC Cancer*. (2018) 18: 267. |
| Pancreatic cancer | Tao Jiang et al. Comprehensive evaluation of NT5E/CD73 expression and its prognostic significance in distinct types of cancers. *BMC Cancer*. (2018) 18: 267. |
| Renal carcinoma | Tao Jiang et al. Comprehensive evaluation of NT5E/CD73 expression and its prognostic significance in distinct types of cancers. *BMC Cancer*. (2018) 18: 267. |
| Oral cancer | Tao Jiang et al. Comprehensive evaluation of NT5E/CD73 expression and its prognostic significance in distinct types of cancers. *BMC Cancer*. (2018) 18: 267. |

-continued

| Cancer | Publication |
| --- | --- |
| Lung cancer | Tao Jiang et al. Comprehensive evaluation of NT5E/CD73 expression and its prognostic significance in distinct types of cancers. *BMC Cancer*. (2018) 18: 267. |
| Colon adenocarcinoma | Zhang B, et al. The expression and clinical significance of CD73 molecule in human rectal adenocarcinoma. Tumour Biol. 2015; 36(7): 5459-5466. |
| Melanoma | Wang H, Lee S, Nigro CL et al. NT5E (CD73) is epigenetically regulated in malignant melanoma 954 and associated with metastatic site specificity. Br J Cancer 106(8), 1446-1452 (2012). Tao Jiang et al. Comprehensive evaluation of NT5E/CD73 expression and its prognostic significance in distinct types of cancers. *BMC Cancer*. (2018) 18: 267. |
| Lymphoma | Wang X et al. Tumor CD73/A2aR adenosine immunosuppressive axis and tumor-infiltrating lymphocytes in diffuse large B-cell lymphoma: correlations with clinicopathological characteristics and clinical outcome Int J Cancer 2019 Sep 1; 145(5): 1414-1422. |

The term "antibody" recited herein includes a polyclonal antibody, a monoclonal antibody, a single chain antibody fragment, a bispecific antibody, a single-domain antibody, a nanobody, a chimeric antibody, or a partially or fully humanized antibody. The methods for generating an antibody reactive with a specific antigen are known in the art. For example, the antibody can be generated by recombinant methods, or by immunizing an animal with the antigen or an antigen-encoding nucleic acid.

A typical IgG antibody comprises two heavy chains and two light chains inter-connected by disulfide bonds. Each heavy chain has a constant domain (i.e., "$C_H$" or "CH") and a variable domain (i.e., "$V_H$" or "VH"). Each light chain has a constant domain (i.e., "$C_L$" or "CL") and a variable domain (i.e., "$V_L$" or "VL"). Each $V_H$ and $V_L$ is composed of three complementarity-determining regions (CDRs) and four framework regions (FRs), wherein the CDRs are hypervariable and the FRs are more conserved, arranged from amino-terminus to carboxy-terminus in the following order: FR1, CDR1, FR2, CDR2, FR3, CDR3, and FR4. The CDRs are primarily responsible for binding an epitope of an antigen. In certain embodiments of the present invention, the antibody comprises a fragment derived from IgG1, IgG2, IgG3, or IgG4. For example, in certain embodiments of the present invention, the antibodies comprise a fragment of the variable domain of IgG1, IgG2, IgG3, or IgG4.

The term "epitope" is the site on the antigen to which an antibody binds. U.S. Pat. No. 9,938,356B2 mentions an antibody that is capable of binding CD73 on epitopes such as positions 206 and 211 (The positions of 206 and 211 are the same positions of 180 and 185 described in U.S. Pat. No. 9,938,356B2 since the signal peptide sequence comprising 26 amino acids in the CD73 sequence was removed). Different from U.S. Pat. No. 9,938,356B2, the antibodies of the present invention bind to the CD73 on at least one of the glutamic acid residue at position 296 and the arginine residue at position 297.

The positive control (i.e., Oleclumab) used in the embodiments described in this specification was synthesized by the inventors and has an amino acid sequence the same as that of MEDI9447 disclosed by U.S. Pat. No. 9,938,356B2.

The term "antigen-binding fragment" of an antibody, and the like, as used herein, includes any naturally occurring, enzymatically obtainable, synthetic, or genetically engineered polypeptide or glycoprotein that specifically binds an antigen to form a complex. An antigen-binding fragment of an antibody may be derived, e.g., from a full antibody molecule using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

An antigen-binding fragment of an antibody typically comprises at least one variable domain. The variable domain may be of any size and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL, or VL-VL dimers. A linker may consist of at least 2 (e.g., 5, 10, 15, 20, 40, 60, or more) amino acids, and thus result in a flexible or semi-flexible linkage between adjacent VH and/or VL domain in a single polypeptide molecule. Alternatively, the antigen-binding fragment of an antibody may contain a monomeric VH or VL domain.

In certain embodiments, an antigen-binding fragment of an antibody may contain at least one variable domain covalently linked to at least one constant domain, and the variable and constant domains may be either directly linked to one another or can be linked by a linker. A linker may consist of at least 2 (e.g., 5, 10, 15, 20, 40, 60, or more) amino acids, and thus result in a flexible or semi-flexible linkage between adjacent variable and/or constant domains in a single polypeptide molecule. Moreover, the antigen-binding fragment of an antibody may comprise a homo-dimer or hetero-dimer (or other multimers) of any of the variable and constant domain configurations in non-covalent association with one another and/or with one or more monomeric VH or VL domain (e.g., by a disulfide bond(s)).

In certain embodiments, the antibody or antigen-binding fragment thereof in accordance with the present invention may also link with a drug conjugate to form an antibody-drug conjugate (ADC), or further links with a second antibody or a second antigen binding fragment to form a bispecific antibody.

In other embodiments, the antibody in accordance with the invention is a humanized antibody. A "humanized antibody" refers to a recombinant protein in which the CDRs from an antibody from one species (e.g., a rodent antibody) are transferred from the heavy and light chains of the species (rodent antibody) into human heavy and light domains, including human framework region (FR) sequences. The constant domains of the antibody molecule are derived from those of a human antibody.

The term "% identity" as used herein is defined as the percentage of amino acid residues or nucleotides in a candidate sequence that is identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity.

As mentioned above, inventors of the present invention found novel anti-CD73 antibodies that comprise specific complementarity-determining regions (CDRs) and are effective in inhibiting CD73. As compared to the positive control (i.e., Oleclumab), the antibodies and antigen-binding fragments in accordance with the present invention have a better CD73-binding activity, a longer effective duration of inhibiting AMP consumption, and a better effect on activating immune cells and inhibiting tumor growth.

Therefore, the present invention relates to a novel antibody or an antigen-binding fragment thereof, comprising: (i) a heavy chain variable domain comprising a HCDR1 region, a HCDR2 region, and a HCDR3 region, wherein the HCDR1 region comprises an amino acid sequence of SEQ ID NO: 4 with at most one variation, the HCDR2 region comprises an amino acid sequence of SEQ ID NO: 5 with at most one variation, and the HCDR3 region comprises an amino acid sequence of SEQ ID NO: 6 with at most one variation; and; and (ii) a light chain variable domain comprising a LCDR1 region, a LCDR2 region, and a LCDR3 region, wherein the LCDR1 region comprises an amino acid sequence of SEQ ID NO: 7 with at most one variation, the LCDR2 region comprises an amino acid sequence of SEQ ID NO: 8 with at most one variation, and the LCDR3 region comprises an amino acid sequence of SEQ ID NO: 9 with at most one variation.

Inventors of the present invention also found that the antibodies and antigen-binding fragments in accordance with the present invention can specifically bind to human CD73 on at least one of the glutamic acid residue at position 296 and the arginine residue at position 297. Accordingly, the present invention also relates to a novel antibody or an antigen-binding fragment thereof that specifically binds to human CD73 on at least one of the glutamic acid residue at position 296 and the arginine residue at position 297.

The present invention also relates to a nucleic acid molecule encoding the antibody or antigen-binding fragment thereof as described above; a vector comprising the nucleic acid molecule as described above; a recombinant host cell comprising a nucleic acid molecule and/or a vector as described above; a pharmaceutical composition comprising (i) an antibody or antigen-binding fragment thereof as described above, a nucleic acid molecule encoding the aforesaid antibody or antigen-binding fragment thereof, a vector comprising the aforesaid nucleic acid molecule, a recombinant host cell comprising the aforesaid nucleic acid molecule, or a recombinant host cell comprising the aforesaid vector, and (ii) a pharmaceutically acceptable carrier; a method of inhibiting CD73, comprising administering a subject in need thereof an effective amount of the pharmaceutical composition as described above; use of the antibody or antigen-binding fragment thereof as described above in the manufacture of a medicament for inhibiting CD73; and use of the antibody or antigen-binding fragment thereof as described above for inhibiting CD73.

The pharmaceutical composition or medicament in accordance with the present invention can be used for systemic or topical administration and can be delivered by various drug delivery systems (DDSs), such as an oral drug delivery system, a transdermal drug delivery system, a transmucosal drug delivery system, or an injectable drug delivery system. For example, to enhance bioavailability, control drug release speed, target the lesion precisely, and/or reduce side effects, the pharmaceutical composition or medicament can be delivered by a liposome, a microcapsule, nanoparticles, or microneedles, but is not limited thereby.

Depending on the desired purpose(s), the pharmaceutical composition or medicament in accordance with the present invention can be provided in any suitable form without particular limitations. For example, the pharmaceutical composition or medicament can be provided in a form for oral administration, intravenous injection (including drip infusion and bolus injection), intramuscular injection, subcutaneous injection, intraarterial injection, intraperitoneal injection, transdermal administration (such as a patch), or transmucosal administration (such as nasal spray, nasal drops, and suppository), but is not limited thereby. Depending on the form and purpose(s), a suitable carrier can be chosen and used to provide the pharmaceutical composition or medicament, wherein the carriers are known in the art of pharmaceutical engineering. Examples of the carrier include, but are not limited to, excipients, diluents, fillers, buffers, auxiliaries, stabilizers, absorption enhancers, disintegrating agents, hydrotropic agents, antioxidants, adhesives, binders, tackifiers, dispersants, suspending agents, lubricants, and hygroscopic agents.

As a form for oral administration, the pharmaceutical composition or medicament in accordance with the present invention can be provided by any suitable methods in any suitable form for oral administration, wherein the liquid form suitable for oral administration includes syrups, an oral solution, a suspension, and an elixir, and the solid form suitable for oral administration includes a powder, a granule, a troche, a dragee, an enteric-coated tablet, a chewable tablet, an effervescent tablet, a film-coated tablet, a capsule, and a long-acting slow-release tablet. The pharmaceutical composition or medicament provided in accordance with the present invention can comprise any pharmaceutically acceptable carrier that will not adversely affect the desired effects of the active ingredient (i.e., antibodies of the present invention or antigen-binding fragment thereof). For example, the pharmaceutically acceptable carriers for the aforesaid liquid form include but are not limited to, water, saline, dextrose, glycerol, ethanol or its analogs, oil (e.g., olive oil, castor oil, cottonseed oil, peanut oil, corn oil, and germ oil), glycerol, polyethylene glycol, and combinations thereof, and the pharmaceutically acceptable carriers for the aforesaid solid form include, but are not limited to, cellulose, starch, kaolinite, bentonite, sodium citrate, gelatin, agar, carboxymethyl cellulose, gum arabic, tragacanth, seaweed gel, glyceryl monostearate, calcium stearate, colloidal silicon dioxide, and combinations thereof.

As a form for transdermal administration, the pharmaceutical composition or medicament in accordance with the present invention can also comprise any pharmaceutically acceptable carrier that will not adversely affect the desired effects of the active ingredient (i.e., antibodies of the present invention or antigen-binding fragment thereof), such as water, mineral oil, propylene glycol, polyethylene oxide, liquid petrolatum, sorbitan monostearate, and polysorbate 60. The pharmaceutical composition or medicament can be provided by any suitable methods in any suitable form for transdermal administration, such as in the form of a patch (such as a microneedle patch), but is not limited thereby.

As for the form of injections or drips, the pharmaceutical composition or medicament can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition or medicament as an intravenous infusion, an emulsified intravenous infusion, a powder for injection, a suspension for injection or a powder suspension for injection. Alternatively, the pharmaceutical composition or medicament can be prepared as a pre-injection solid. The desired injection is provided by dissolving the pre-injection solid in other solutions or suspensions or emulsifying it before being administered to a subject in need.

As a form for transmucosal administration, the pharmaceutical composition or medicament can comprise one or more ingredient(s), such as a penetrant, a surfactant, a viscosity regulator, a pH-adjusting agent, a preservative, a stabilizer, an osmo-regulator, and other carriers to provide the pharmaceutical composition or medicament as eye drops, an ointment, orally disintegrating tablets, a nasal spray, nasal drops, or a suppository.

Optionally, the pharmaceutical composition or medicament in accordance with the present invention can also comprise a suitable amount of additives, such as a toner or a colorant for enhancing the visual perception of the pharmaceutical composition or medicament, and/or a buffer, a conservative, a preservative, an antibacterial agent, or an antifungal agent for improving the stability and storability of the pharmaceutical composition or medicament.

The pharmaceutical composition or medicament provided in accordance with the present invention can optionally further comprise one or more other active ingredient(s) (such as PD-1 antagonist, PD-L1 antagonist, CTLA-4 antagonist, EGFR inhibitor, and A2AR inhibitor) to further enhance the effects of the pharmaceutical composition or medicament or to increase the application flexibility and application adaptability of preparation thus provided, as long as the other active ingredients do not adversely affect the desired effects of the active ingredient of the present invention (i.e., antibodies of the present invention or antigen-binding fragment thereof).

The present invention also provides a method of inhibiting CD73, comprising administering a subject in need thereof an effective amount of the antibody or antigen-binding fragment thereof as described above, wherein the term "a subject in need thereof" refers to a subject having weak immune system and/or suffering from cancer, especially the cancer with high expression of CD73. Preferably, the aforementioned cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma, and lymphoma. In the method in accordance with the present invention, the antibody or antigen-binding fragment thereof could be administered to the subject in need as a form of the pharmaceutical composition or medicament as described above, and the administration type, administration route, administration form, administration frequency and uses of the pharmaceutical composition and the medicament are also all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLE

Example 1: Preparation of Anti-CD73 Antibodies 1-1. Construction of scFv Antibody Library Recombinant Human CD73-6×His having an amino acid sequence of SEQ ID NO: 1 was used as an antigen to immunize a mouse once a week for 6 to 9 times. After immunization, the mouse was sacrificed and the spleen and lymph nodes thereof were obtained. Total RNAs of the spleen and lymph nodes were extracted and reverse-transcribed in an RT-PCR procedure with the primers to construct antibody fragments containing VH and VL. The antibody fragments were assembled into scFv fragments in polymerase chain reaction (PCR), and a scFv library was constructed.

1-2. Preparation of scFv Phage for Bio-Panning

The scFv library provided by Example 1-1 was inoculated into a 2×YT medium containing 100 μg/ml ampicillin and 2% glucose (2YTAG) and incubated by shaking at 37° C. until the OD at 600 nm reaches 0.5. The culture was infected with a helper phage and then cultured without shaking in a 37° C. water bath for 30 min. The cells in the culture were collected and suspended in a 2×YT medium containing 100 μg/ml ampicillin and 25 μg/ml kanamycin (2YTAK) and further incubated with shaking at 30° C. overnight. The supernatant of the culture was collected and mixed with ⅕ volume of PEG/NaCl (20% Polyethylene glycol 8000, 2.5 M NaCl) and stayed at 4° C. for at least one hour. After centrifuging, the pellet was collected and suspended in PBS and spun again to collect the supernatant.

1-3. Bio-Panning of ScFv Phages by Using ELISA Method

An ELISA plate (Nunc) was coated with 5 to 25 μg/100 μl of antigen per well and stayed in sodium bicarbonate buffer (pH 9.6) at 4° C. overnight. The wells were washed 3 times with PBS and blocked with 300 μl of 5% skim milk-containing PBS (MPBS) per well at 37° C. for 2 hours. After being washed 3 times with PBS, 100 μl of phages in 5% MPBS with his-tag-containing fusion protein were added and incubated at 37° C. for 90 min. After being washed 4 to 10 times with 0.05% Tween 20-containing PBS (PBST) and 4 to 10 times with PBS, the phages were eluted by adding 100 μl of 100 mM triethylamine (TEA) and reacted at 37° C. for 20 min. 100 μl of eluted phages were neutralized with 50 μl of 1 M Tris, pH 7.4. 3 mL of TG1 at an exponentially growing stage were added with the eluted phages. The cultures were incubated at 37° C. for 30 min without shaking for infection. The infected TG1 bacteria were added with 20 mL of 2×YT-AG and then incubated at 37° C. overnight.

1-4. Preparation of Next Round Phage

The cultures provided by Example 1-3 were spun, collected, and then suspended in 0.5 mL of 2×YT-AG, 15% glycerol. Then, 10 μl of the bacteria were added to 10 mL of 2×YT-AG and the bacteria grew with shaking at 37° C. until the OD at 600 nm reaches 0.5. 10 mL of the culture was infected with M13KO7 helper phage by adding the helper phage at a ratio of 1:20 (M13KO7 helper phage: culture) and the infected culture was incubated without shaking in a 37° C. water bath for 30 min. The cultures were spun to collect the pellet, and the pellet was suspended with 25 mL of 2×YT-AK and then cultured at 30° C. overnight. Further, 25 mL of the overnight culture was spun at 10,000 rpm for 20 min to collect the supernatant, and ⅕ volume (5 mL) PEG/NaCl was added to the supernatant to provide a mixture. The mixture was spun at 10,000 rpm for 20 min and the pellet was collected and suspended in 0.5 mL PBS.

1-5. Screening of Human CD73-Positive Phage Clones by ELISA

The suspensions provided by Example 1-4 were spread on a plate, and cultured to obtain individual colonies. The individual colonies thus provided were inoculated into 200 μl of 2×YT-AG 96-well plates and grew with shaking at 37° C. overnight, and then 10 μl of the culture was transferred to a second 96-well plate containing 180 μl of 2×YT-A per well for shaking at 37° C. for 2 hours. Then, 50 μl of 2×YT-A with $2.4 \times 10^{10}$ pfu/mL M13KO7 helper phage was added to each well of the second plate to provide a mixture. The mixture was shaken at 37° C. for 2 hours. 50 μl of 2×YT-AK3 (the kanamycin concentration was 300 μg/mL) was added to the mixture, and then grew with shaking at 30° C. overnight. The culture was added with 501 MPBS to provide a phage mixture, and 100 μl of the phage mixture was taken for phage ELISA.

The ELISA plates were coated with 1 μg/mL of protein antigen per well, and then rinsed 3 times with PBS and blocked with 300 μl of 5% MPBS per well at 37° C. for 2 hours. After rinsing a further 3 times with PBS, 100 μl phage mixture as detailed above was added and incubated at 37° C. for 90 min. The phage solution was discarded and the wells were washed 6 times with PBST and 6 times with PBS, and then, an appropriate diluted HRP-anti-M13 antibody in 5% MPBS was added to provide a mixture. The mixture was incubated at 37° C. for 60 min, and then washed 6 times with PBST. The wells were developed with substrate solution (TMB) and the reactions were stopped by adding 100 μl of 1 M Hydrochloric acid. The color turned yellow, and the OD at 650 nm and at 450 nm was assayed.

After screening, a total of 317 clones were identified with different CDR sequences.

1-6. The Monoclonal Phage Preparation

The 317 clones provided by Example 1-5 were subjected to the procedure as follows. The bacteria were cultured at 37° C. overnight. Thereafter, 100 μl bacteria were added with 2×YT-AG, and the bacteria grew with shaking at 37° C. until the OD at 600 nm reaches 0.5. 10 mL of the culture was infected with M13K07 helper phage by adding the helper phage at a ratio of 1:20 (M13KO7 helper phage: culture), and the infected culture was incubated without shaking in a 37° C. water bath for 30 min. The cultures were spun to collect the pellet, and the pellet was suspended with 25 mL of 2×YT-AK and then cultured at 30° C. overnight. Further, 25 mL of the overnight culture was spun at 10,000 rpm for 20 min to collect the supernatant, and ⅕ volume (5 ml) PEG/NaCl was added to the supernatant to provide a mixture. The mixture was spun at 10,000 rpm for 20 min, and the pellet was collected and suspended in 0.5 mL PBS.

1-7. Screening CD73 Phage Binding to KLM-1 Cells

To screen the phage clones that can bind to CD73 expressing cells, KLM-1 cells were mixed with anti-CD73 phages provided by Example 1-6 ($10^{11}$ virions/tube, 100 μl). After incubation at 4° C. for 1 hour, the cells were washed and centrifuged, and were reacted with anti-M13-FITC (1:500) to each tube. After washing and centrifuging, adding 0.3 mL of Flow Cytometry Staining Buffer to each tube. Mixing gently and analyzing by BD FACSVerse™ Flow Cytometer.

After being analyzed by flow cytometry, 27 phage clones were shown to have the function of binding to the CD73 expressing cells, KLM-1.

Then, as described in Example 1-8 as follows, a full-length antibody was expressed by further constructing the VH and VL chains of these CD73 binding phage clones into a full-length antibody expression vector.

1-8. Expression of Full-Length Antibodies

The genes encoding anti-human CD73 antibodies were constructed by inserting the VH and VL chains, which come from the scFv phage clones provided by Example 1-7, into an expression vector containing CH and CL chain, respectively. Free-style 293 cells were transfected with the constructed vector. The antibodies were purified by using Protein A Sepharose Fast Flow (GE Healthcare, 17-1279-02). After purification, the antibodies were quantified by measuring at OD 280 nm and checked by reducing and non-reducing PAGE.

1-9. Binding Affinity Assay by Using ELISA

An ELISA plate was coated with 100 μl per well of human CD73 at 4° C. overnight, and then rinsed 3 times with PBS and blocked with 300 μl per well of 5% MPBS at 37° C. for 2 hours. The wells were rinsed 3 times with PBS, and 100 μl of anti-human CD73 antibody (with 2-fold serial dilutions) was added thereinto and incubated at 37° C. for 90 min. The test solution was discarded and washed 3 times with PBS. Appropriately diluted antibodies provided by Example 1-8 in 5% MPBS (1:10000) were added to the wells, and the wells were incubated at 37° C. for 60 min, and then the wells were washed 3 times with PBS. The wells were developed with 100 μl of substrate solution TMB and the reactions were terminated by adding 50 μl of 1 M sulfuric acid sulphuric acid. The color turned yellow and the OD at 650 nm and at 450 nm were assayed.

The binding affinity value ($K_D$) of antibodies provided by Example 1-8 was calculated by the equation of one site binding (hyperbola) of the GraphPad Prism software. The antibody whose $K_D$ was smaller than $10^{-9}$M was chosen for the next functional assay of the cellular CD73 activity inhibition.

Example 2: Selecting the Antibody with a Better Effect of Inhibiting CD73 Function To investigate the inhibitory effect of selected antibodies on CD73 activity in CD73 highly expressing cells, the following experiments were conducted by using the AMP consumption assay as the method from Hay et al (Oncoimmunology 2016, 5, 1208875). It has been known that AMP can inhibit the ability of ATP in emitting luminescence. Thus, the consumption of AMP can be determined by measuring the luminescence level. Furthermore, AMP can be converted into adenosine by the membrane protein CD73, thus, the lower luminenscence level, the lower AMP consumption, and the higher the inhibitory effect of the antibody on the CD73. MDA-MB-231 cells were previously seeded into a 96-well plate ($2.5 \times 10^3$ cells/well) for 16 hr, and then cells in each well were treated with the following conditions: cells cultured with L-15 medium containing 100 μM AMP and antibody (8 concentrations with serial dilution) in each group, including isotype IgG, Oleclumab, and selected antibodies, at 37° C. incubator for 24 hours, supernatants of each group were collected into round-bottom 96-well plate, and then ATP was added into in a final concentration of 100 M. There are several control treatments: the "Cell+ATP" group means that cells were only cultured with L-15 medium without antibody and AMP, and then ATP was added thereinto; the "Cell+AMP+ATP" means that cells were cultured with L-15 medium containing 100 μM AMP, and then ATP was added thereinto; the "ATP only" means L-15 medium without cells incubation, and then ATP was added thereinto; the "AMP+ATP" means medium containing 100 μM AMP without cells incubation, and then ATP was added thereinto.

After the above procedure was completed, the medium of each group was mixed with Celltiter-glo reagent at a volume ratio of 1:1 and incubated in the dark for 10 min. Luminometer was used for measuring the luminescence of each group. The CD73 enzymatic activity (i.e., the consumption % of AMP) of each group can be calculated by the below Formula 1, and the results are shown in FIG. 1.

$$\text{consumption \% of } AMP = \frac{\text{luminescence of experimental group} - \text{luminescence of } ATP + AMP \text{ group}}{\text{luminescence of } ATP \text{ only group} - \text{luminescence of } ATP + AMP \text{ group}} \times 100\%$$

Formula 1

2-1. Identify the Antibody which has a Better Inhibiting CD73 Activity Function

After the antibodies selected by both cell-based (flow assay) and antigen (ELISA) binding affinity assays, the next-step were checking the inhibitory effect of these antibodies on CD73 activity by using the AMP consumption assay as described above. All the selected antibodies have no significant better effect on inhibiting CD73 activity than the reference antibody, Oleclumab. But only the 10H5 have the significantly inhibiting CD73 superior than Oleclumab. As shown in FIG. 1A, after 24 hours of culturing MDA-MB-231 cells and 100 μM AMP with reference antibody Oleclumab, the AMP was almost consumed. However, the "10H5" group can significantly inhibit the consumption of AMP, and the consumption of AMP was even reduced to be the lowest level (<20%) when the concentration of 10H5 was higher than 10 nM. These results indicate that, as compared to the Oleclumab, the 10H5 has a superior and better inhibitory (in 24 hours) effect on CD73 activity on MDA-MB-231 cancer cells.

2-2. Confirm the 10H5 with a Novel CD73 Inhibition Function by NSCLC Calu-1 Cells To confirm the 10H5 with a superior inhibitory effect of CD73, the CD73 highly expressing NSCLC Calu-1 was used for testing whether it also works as in MDA-MB-231.

NSCLC Calu-1 cells were seeded into a 96-well plate (500 cells/well), and cultured with McCoy's 5a medium containing 100 μM AMP and antibodies, including isotype IgG, Oleclumab and 10H5 (serial dilution with 8 concentrations), at 37° C., 5% $CO_2$ incubator for 24 hours, and then 100 μM ATP was added thereinto. Other control groups and following procedure are described as above, and the results are shown in FIG. 1B.

Figure 1B:
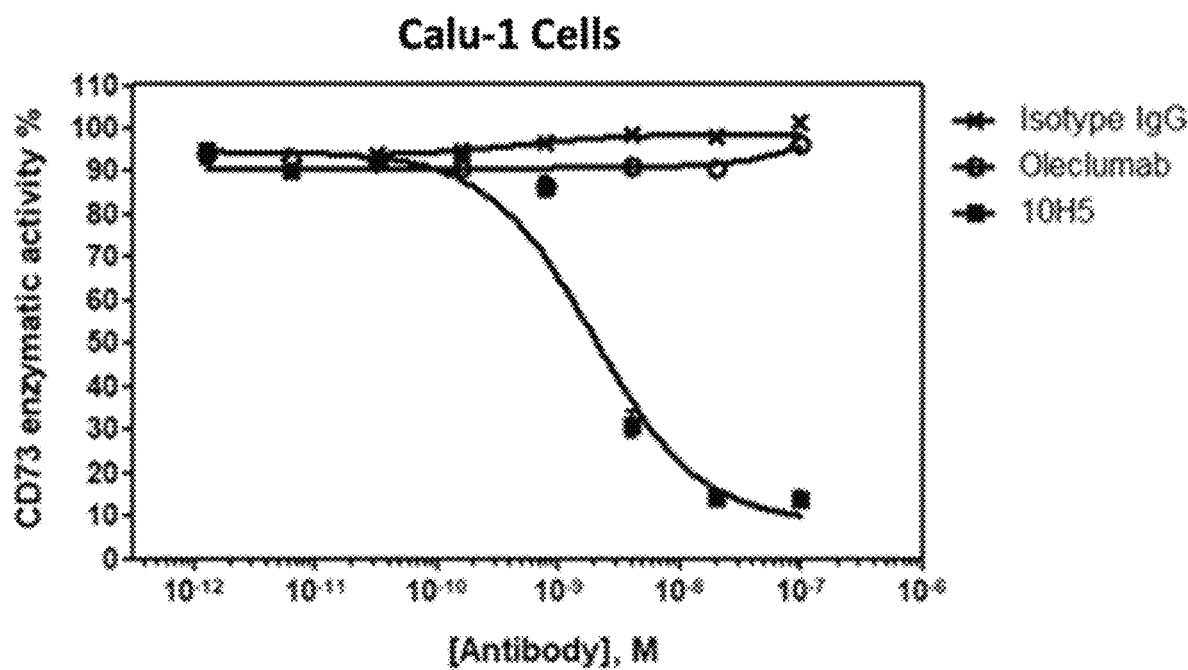
FIG. 1B indicates that the antibody 10H5 also has a superior effect on inhibiting CD73 activity than Oleclumab in Calu-1, a non-small cell lung cancer (NSCLC) cell line.

As shown in FIG. 1B, after 24 hours of culturing, the "Oleclumab" group, the AMP was also almost consumed. However, the "10H5" group can still significantly inhibit the consumption of AMP, and the consumption of AMP was reduced to be even lowest (10%) when the concentration of 10H5 was higher than 10 nM. These results indicate that, as compared to the Oleclumab, the antibody of the present invention, 10H5, has a better inhibitory (in 24 hours) effect on CD73 activity on Calu-1 cancer cells.

Example 3: Humanization of Antibody 3-1. CDR Grafting

Since the 10H5 antibody was found to have a novel and special inhibitory effect on CD73 activity, we humanized the 101H5 antibody for further development as a therapeutic antibody. As described above, the variable region of the 10H5 antibody was derived from the mouse scFv sequence. To make a humanized 10H5 antibody, the framework of 10H5 antibody was replaced with a human framework selected from the IMGT database (www.imgt.org/) (heavy chain: IGHV1-46*01F; light chain: IGKV1-12*01). And, to replace the whole framework of the 10H5 antibody with a human framework, 21 amino acids in the heavy chain and 26 amino acids in the light chain were mutated. Thus, the variation of the heavy chain and the light chain was 25.6% (21 mutations/82 amino acids in the heavy chain) and 34.2% (26 mutations/76 amino acids in the light chain), respectively.

3-2. Back Mutation

Because the framework of humanized antibody may directly or indirectly affect the binding affinity to antigen or the inhibitory effect on CD73 activity. Therefore, some specific amino acid residues on the human framework would need to be mutated back to that of the mouse framework.

3-3. Inhibitory Effect of the Humanized Antibodies on CD73 Activity

The humanized antibodies were selected by three criteria: the binding affinity, the CD73 inhibitory activity, and the minimum number of back mutations. There are three antibodies, HuB9/HdB7, HuB10/HdB6 and HuB10HdB7, which are combined by two heavy chains: HuVHB9 (HuB9) and HuVHB10 (HuB10) and two light chains: HdVLB6 (HdB6) and HdVLB7 (HdB7), that meet these three conditions. The amino acid sequences of HuB9, HuB10, HdB6, and HdB7 were shown in SEQ ID NO: 10 (HuB9), SEQ ID NO: 11 (HuB10), SEQ ID NO: 12 (HdB6), and SEQ ID NO: 13 (HdB7). To further investigate the characters of the humanized antibodies of the present invention, the abilities of HuB9/HdB7, HuB10/HdB6 and HuB10/HdB7 on inhibiting AMP consumption (i.e., inhibiting CD73 activity) were analyzed by the AMP consumption assay as described in Examples 2. The results are shown in FIGS. 2A and 2B.

Figure 2A:
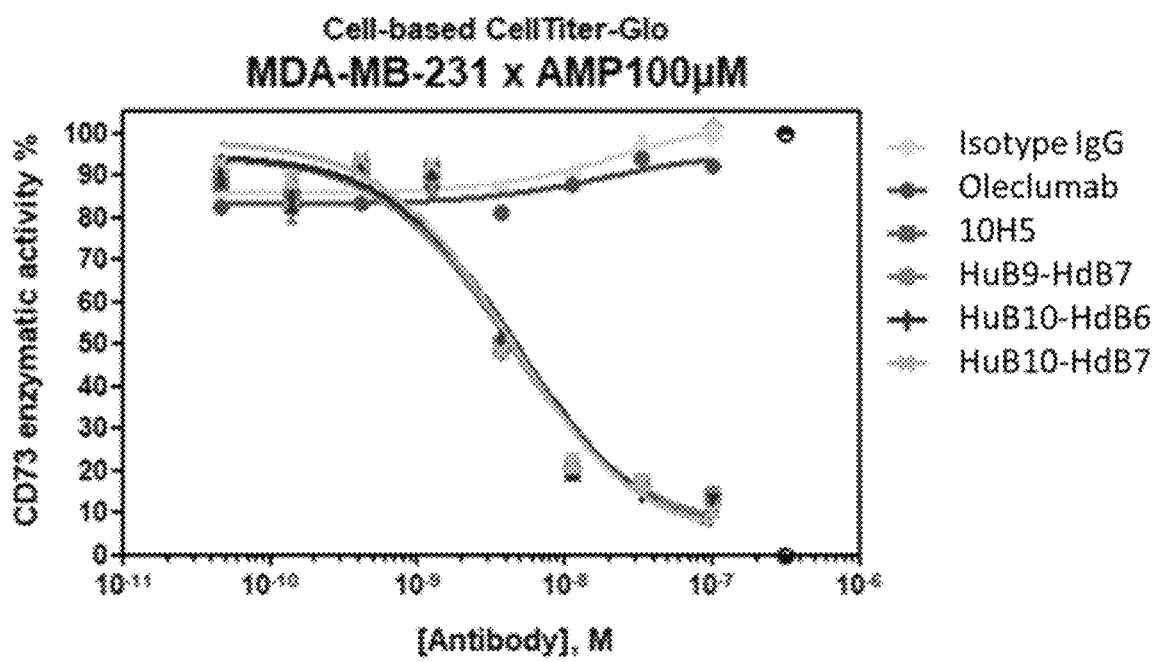
FIGS. 2A and 2B indicate that the antibody of present invention, 10H5 and its humanized derivatives, HuB9/HdB7, HuB10/HdB6 and HuB10/HdB7, have a superior effect on inhibiting CD73 activity than Oleclumab in different cancer cell types (FIG. 2A: MDA-MB-231 cells.
Figure 2B:
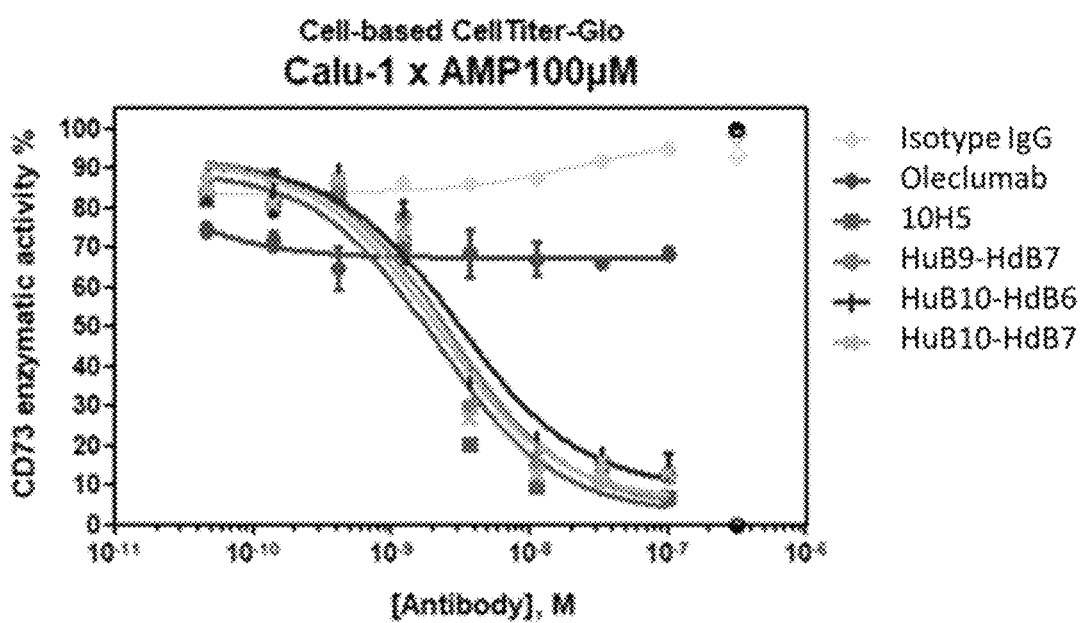

As shown in FIGS. 2A and 2B, HuB9/HdB7, HuB10/HdB6 and HuB10/HdB7 can provide a similar inhibitory effect on AMP consumption as 10H5 antibody on the MDA-MB231 (FIG. 2A) and Calu-1 (FIG. 2B) cells.

Example 4: Binding Affinity of the Antibodies of the Present Invention

To investigate the characters of the antibodies of the present invention, including 10H5 and its humanization derivatives, HuB9/HdB7, HuB10/HdB6 and HuB10/HdB7, we analyzed the binding affinity of these antibodies by Biacore SPR.

The analyzing condition was flow rate 30 μL/min, associate time 180 s, dissociate time 600 s; the concentrations of 10H5 antibody were 0.625 nM, 1.25 nM, 2.5 nM, 5 nM and 10 nM). The binding affinity of 10H5 and its humanization derivatives HuB9/HdB7, HuB10/HdB6 and HuB10/HdB7 are shown in FIGS. 3A, 3B, 3C and 3D, respectively.

Figure 3A:
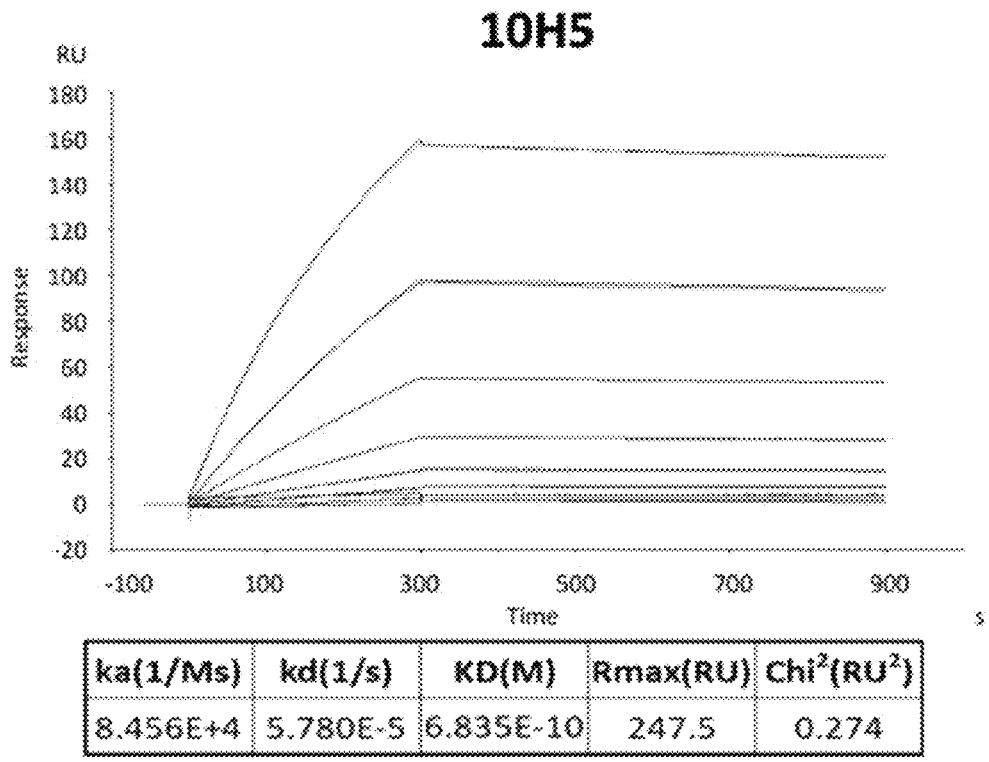
FIGS. 3A to 3D show the Biacore SPR results of the binding affinity of the antibodies of the present invention, 10H5 (FIG. 3A) and its humanized derivatives, HuB9/HdB7 (FIG. 3B), HuB10/HdB6 (FIG. 3C) and HuB10/HdB7 (FIG. 3D), to human CD73 antigen.
Figure 3B:
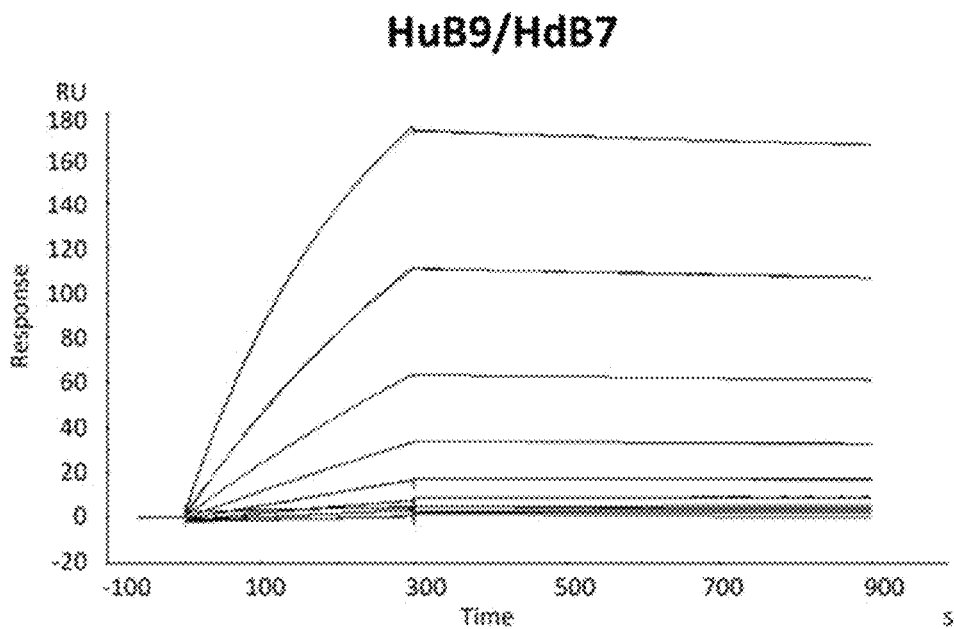
Figure 3C:
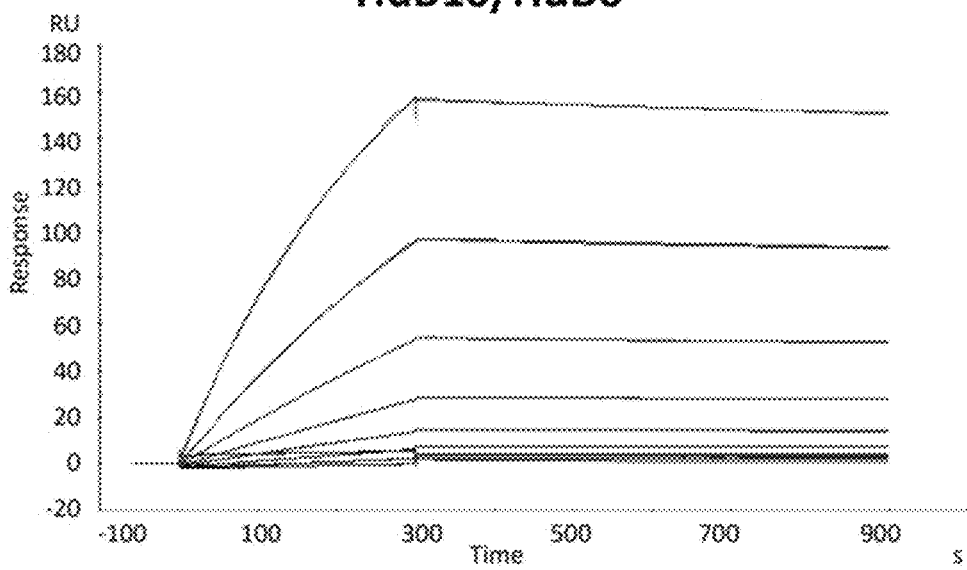
Figure 3D:
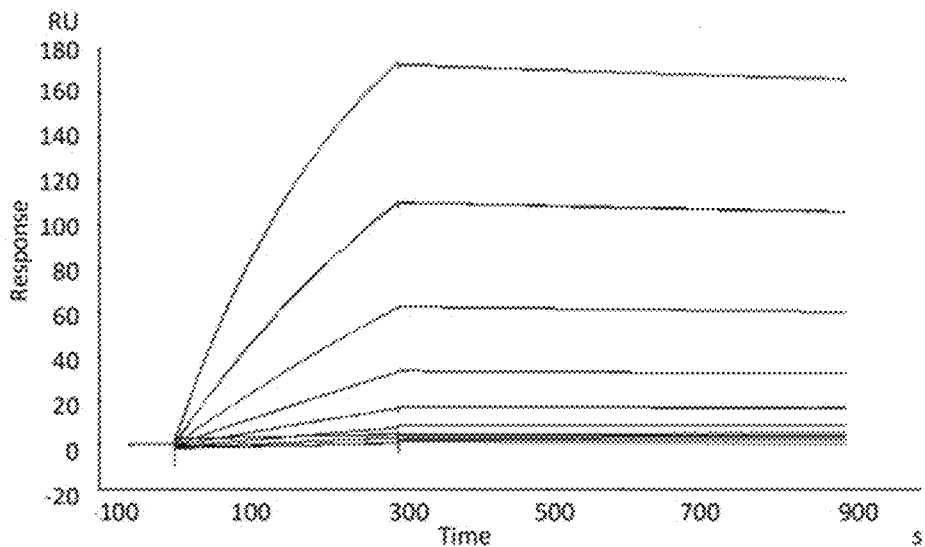

As shown in FIG. 3A, the KD value of 10H5 antibody measure by Biacore SPR was $6.835 \times 10^{-10}$ M. As shown in FIGS. 3B, 3C and 3D, the KD value of HuB9/HdB7, HuB10/HdB6 and HuB10/HdB7 antibodies measured by Biacore SPR was 6.227, 8.028 and 6.781×10$^{-10}$M, respectively. All the three humanized antibodies have a similar binding affinity to human CD73 as parental 10H5 antibody.

Example 5: Long-Lasting Inhibitory Effect of the Antibodies of the Present Invention on CD73 Activity To further check the antibodies of the present invention have the more long-lasting inhibitory effect on CD73 than oleclumab, we treated the antibodies, 10H5 and its humanized derivatives with both MDA-MB-31 and Calu-1 cells. After 6 and 24-hours treatment, the inhibitory effect was analyzed by AMP consumption assay. The experimental operation method and process are the same as the Example 2, but the antibody concentration was only 10 nM, and the incubation time was 6 hr and 24 hr. The CD73 activity results were presented in FIG. 4A and FIG. 4B.

Figure 4A:
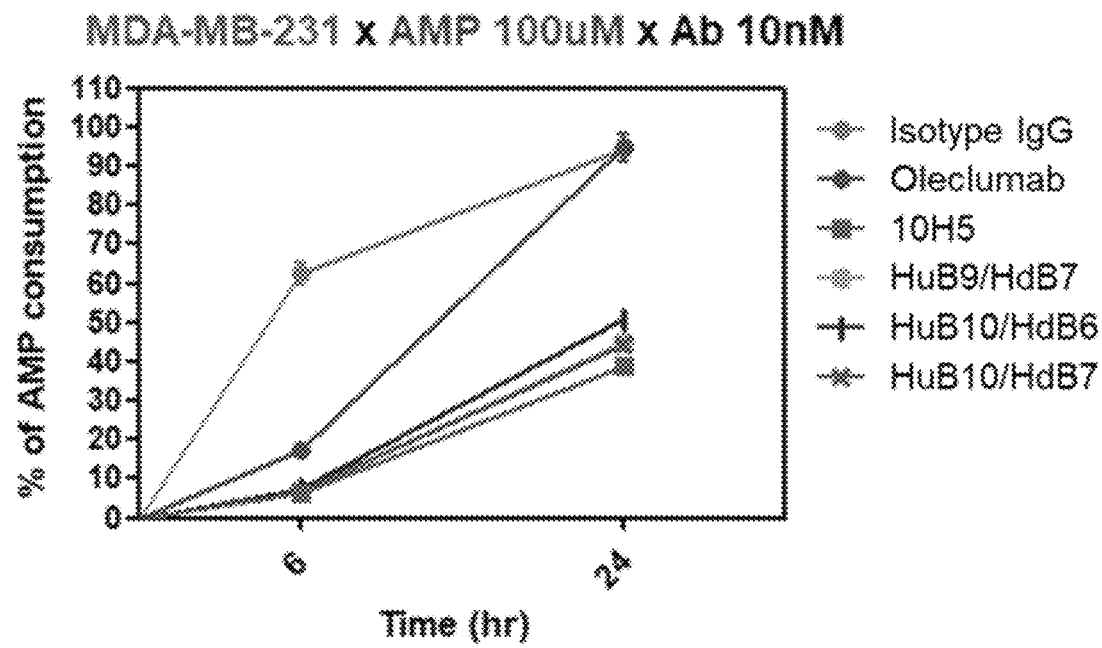
FIGS. 4A and 4B indicate the antibodies of the present invention, 10H5 and its humanized derivatives, HuB9/HdB7, HuB10/HdB6 and HuB10/HdB7, have a more long-lasting inhibitory activity against CD73 compared to Oleclumab (FIG. 4A: MDA-MB-231 cells.
Figure 4B:
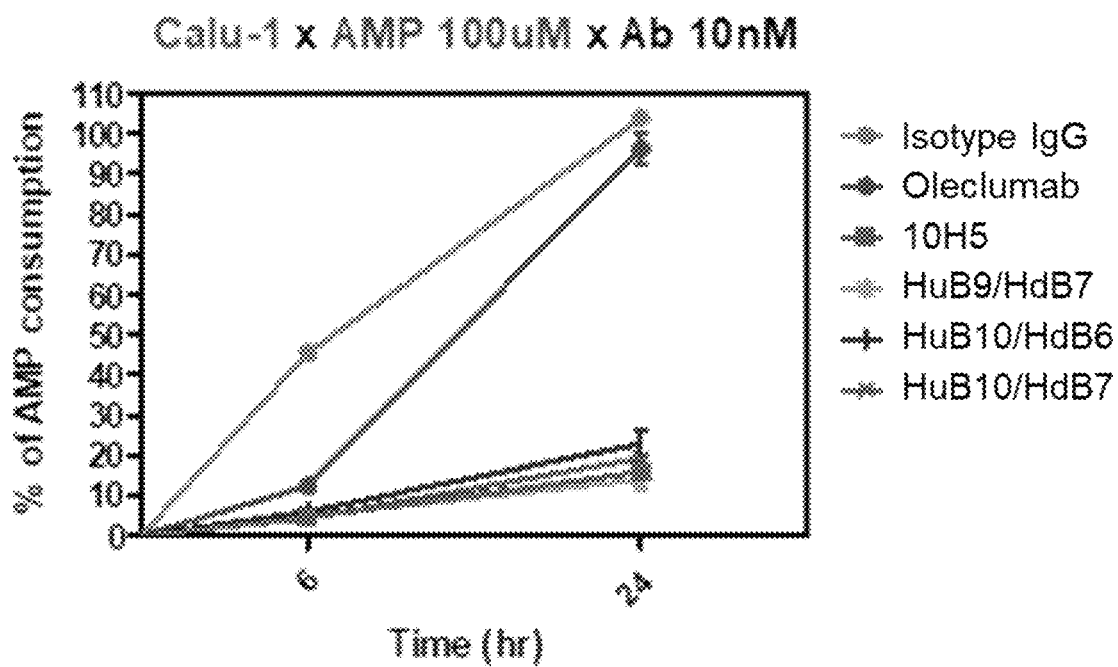

As shown in the FIG. 4A, after 6 hr of the MDA-MB-231 cells treated with AMP and antibody, the AMP consumption was obviously found in the "isotype IgG" group (about 60%). But the AMP consumption was less inhibited by all the antibodies treatment, including "Oleclumab" (less than 20%), "10H5" and its derivatives (less than 10%). However, after 24 h, the AMP of the "Oleclumab" was seen almost consumed completely (above 90%). But the "10H5" and its derivatives were found significantly less AMP consumption (less than 50%) than "Oleclumab" in the MDA-MB-231 cancer cells. As shown in the FIG. 4B, the same tendency result was present in the data of Calu-1 cells, after 6-hr, the AMP was also seen less consumption in "Oleclumab" and 10H5 series, but after 24 hrs, the AMP of the "Oleclumab" was seen almost consumed (above 90%). However, the "10H5" and its derivatives were found significantly less AMP consumption (<20%) than Oleclumab in the Calu-1 NSCLC cells. These results indicate that the antibodies of the present invention, 10H5 and its humanized derivatives, have significantly better and more long-lasting inhibitory property on CD73 activity than Oleclumab.

Example 6: Analyzing the Inhibitory Effect of the Antibodies of the Present Invention on CD73 Activity by Measuring Extracellular AMP Concentration The AMP consumption measured in Examples 2, 3 and 5 was inferred from the luminescence levels. To investigate the actual AMP concentration changed by the reaction of CD73 in cells and antibody, the following experiments by measuring the AMP concentration were conducted.

MDA-MB-231 cells were seeded into a 12-well plate (2.5×10$^4$ cells/well), and cells in each well were cultured with 1.5 ml serum-free medium containing 400 µM AMP and 10 nM antibody, including Oleclumab, 10H5 or its derivatives. The following condition is at 37° C. for 6 hours or 24 hours. There are two control groups as follows: The "AMP only" group means the 1.5 ml medium containing 400 µM AMP (without cells); and the "Cell+AMP" group means that cells were cultured with 1.5 ml serum-free medium containing 400 µM AMP without any antibody. After the above procedure was completed, the AMP concentration in the supernatant was measured by LC/MS. The results are shown in FIG. 5

Figure 5:
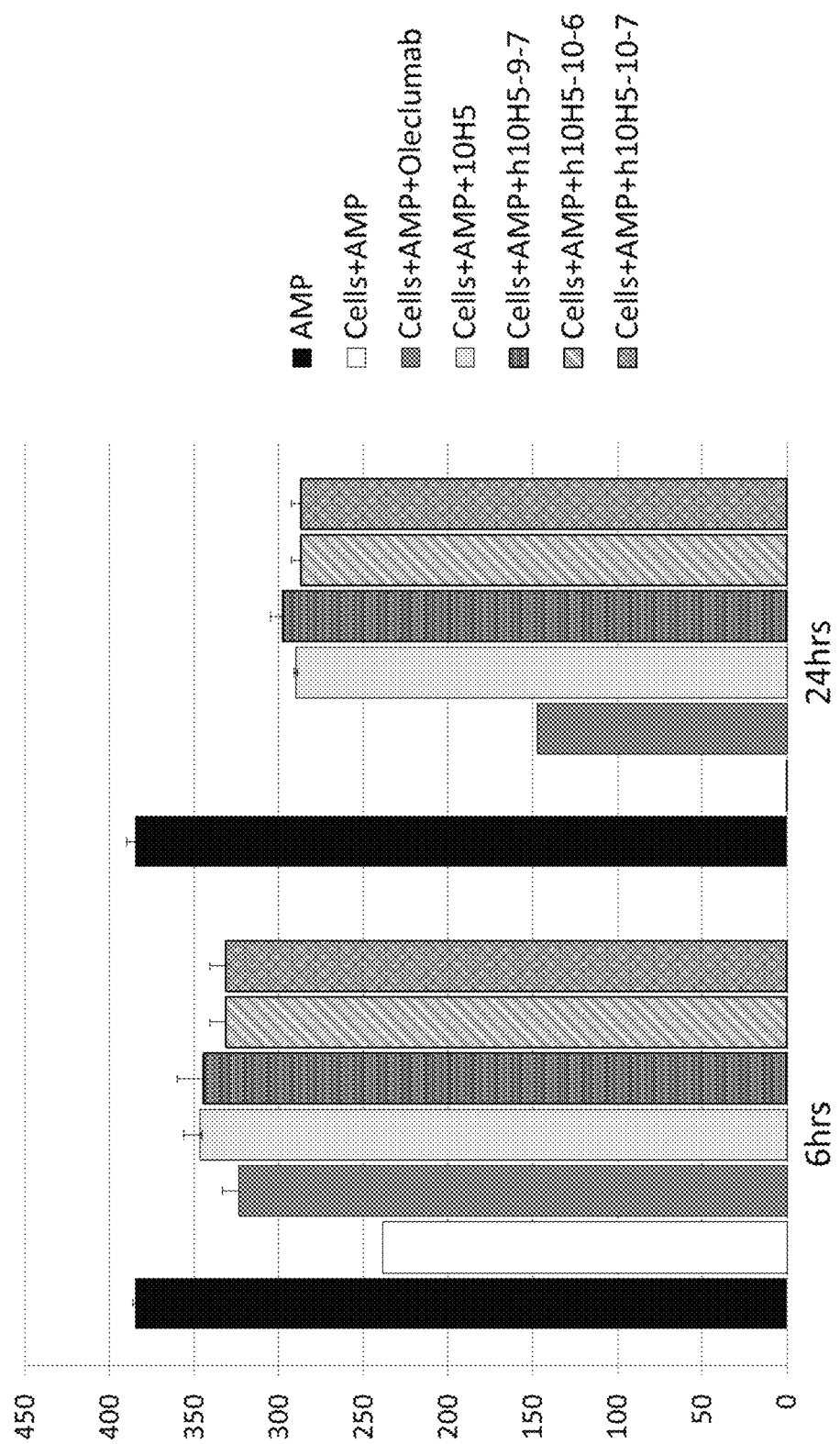
FIG. 5 indicates the antibodies of the present invention, 10H5 and its humanized derivatives, HuB9/HdB7, HuB10/HdB6 and HuB10/HdB7, have a more long-lasting inhibitory activity against CD73 compared to Oleclumab by measuring the actual AMP concentration.

As shown in FIG. 5, after 6 hours of culturing, the AMP concentration of the "AMP only" group was 385 µM, but that of the "Cell+AMP" group was 239 µM, which demonstrated that the MDA-MB-231 cells can consume the AMP in 6 hours. However, the "Cell+AMP+Oleclumab" group (i.e., adding Oleclumab) can maintain an AMP concentration of 324 µM, and the "Cell+AMP+10H5" group (i.e., adding the 10H5 antibody) can maintain an AMP concentration of 347 µM. The humanized antibodies HuB9/HdB7, HuB10/HdB6 and HuB10/HdB7 retained the AMP with almost the same as 10H5, which was 345, 336 and 331 µM, respectively. These results indicate that Oleclumab, 10H5 and its derivatives slightly and equally inhibit the AMP consumption of MDA-MB-231 cells in 6 hours. After 24 hours of culturing, the AMP concentration of the "AMP only" group still maintained at 385 µM, but that of the "Cell+AMP" group was only 0.5 µM, which demonstrated that the MDA-MB-231 cells can consume the entire AMP after 24 hours. The "Cell+AMP+Oleclumab" group (i.e., adding Oleclumab) can only retain the AMP with the AMP concentration of 147 µM. However, the "Cell+AMP+10H5" group (i.e., adding the 10H5 antibody of the present invention) can maintain an AMP concentration of 290 µM. The treatment of humanized antibodies HuB9/HdB7, HuB10/HdB6 and HuB10/HdB7 after 24 hrs also retained the same AMP concentrations as 10H5, which was 298, 286 and 287 µM, respectively. These results indicate that, compared to the Oleclumab, antibodies of the present invention (e.g., 10H5) have significantly better and more long-lasting inhibitory effect on CD73 activity of MDA-MB-231 cells.

Example 7: Activation Effect of the Antibodies of the Present Invention on T-Cells It is known that CD3/CD28 dynabeads can induce the cell division of CD4$^+$ T-cells. 5 Furthermore, the cell division situation can be known by dying the CD4$^+$ T-cells with CFSE and analyzing the fluorescence level of the dyed CD4$^+$ T-cells (the more the cell division occurred, the weaker the fluorescence being emitted, which makes the peak in the flow cytometry chart be left-shifted). To investigate whether the 10H5 antibody of the present invention can activate the immune cells (such as CD4$^+$ T-cell), the following experiments were conducted.

Firstly, 20 mL of human blood was drawn from a donor, and mixed with 20 ml PBS. The blood mixture was slightly added into 50 ml tube containing 15 ml Lymphoprep (STEMCELL Tech.). Centrifuged at 2000 rpm for 30 min without slow down. The thin layer in white color located between the serum and Lymphoprep was PBMC. PBMC was collected and put into a new 50 ml tube. The tube was washed with PBS 3 times, and then CD4$^+$ T-cells in the PBMC were isolated by using a CD4 isolation kit and calculated.

An appropriate number of CD4$^+$ T-cells were collected and centrifuged. Thereafter, 1 µM CFSE was used to stain CD4$^+$ T-cells to evenly make the cell concentration be 1×10$^6$/ml. The cells were then cultured at 37° C. incubator for 20 min and washed with medium 2 times. Thereafter, an appropriate number of cells were collected and centrifuged. The cells were then re-suspended to make the cell concentration to be about 1×10$^6$/ml. The cells were cultured in medium containing 30 IU/mL IL-2, CD3/CD28 dynabeads that equivalent to the numbers of cells, and 10 nM hIgG, Oleclumab, 10H5 or its humanized derivatives, HuB9/HdB7, HuB10/HdB6 or HuB10/HdB7 were added, and cells were cultured in a 37° C. incubator for 60 min and then seeded into a 96-well plate (100 µl/well) with additional 400 µM AMP and cultured in a 37° C. incubator for 3 to 4 days.

The "Control" group means without any CD3/CD28 dynabeads and IL-2 or antibody or AMP were added. The "CD3/CD28" group means that cells were activated by IL-2 and CD3/CD28 dynabeads, but not any antibody or AMP were added after that. The "CD3/CD28/AMP" group means that cells were activated by IL-2 and CD3/CD28 dynabeads, and then cells were cultured for 60 min and seeded into 96 well plated, then added with additional 400 μM AMP and cultured in a 37° C. incubator for 3 to 4 days; After the above procedure was completed, the cells of each group were collected and analyzed with flow cytometry. The results are shown in FIG. 6.

Figure 6:
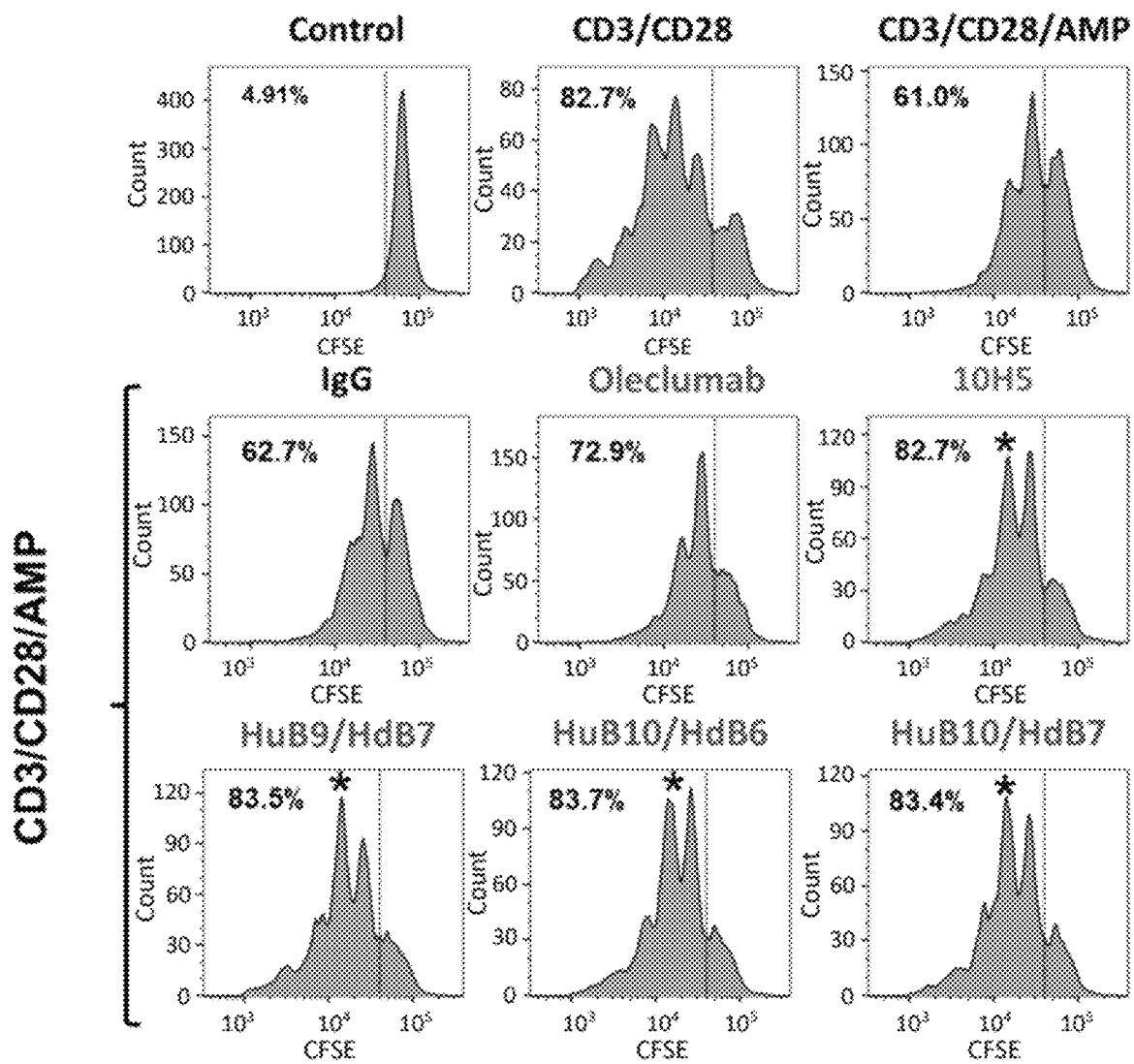
FIG. 6 indicates that the antibodies of the present invention, 10H5 and its humanized derivatives, HuB9/HdB7, HuB10/HdB6 and HuB10/HdB7, are more effective than Oleclumab in reversing the T cell proliferation attenuated by exposure of AMP.

As shown in FIG. 6, after 3 days of culturing, the fluorescence in the "CD3/CD28" group had a left-shift of 82.7%, which was much more than that of the "control" group (4.91%). However, the "CD3/CD28/AMP" group had a left-shift of only 61.0% due to the inhibitory effect of adenosine (which was converted from AMP by the CD73 on the CD4+ T-cells) on cell division. It was also seen when 10 nM of IgG was added before the addition of 400 μM AMP, the level (62.7%) of the left-shift was almost the same as the "CD3/CD28/AMP" group. But, when 10 nM of Oleclumab was added before the addition of 400 μM AMP, it can protect AMP from being converted to adenosine, and thus reverse the left-shift level from 62.7% to 72.9%. Furthermore, the effect of 10H5 with the same dose of 10 nM, the left-shift level was seen from 62.7% to 82.7%, indicating the antibody 10H5 has more efficacy on protecting AMP being converted to adenosine and its ability in reversing the left-shift level is even better than Oleclumab. These results indicate that the antibodies of the present invention (e.g., 10H5) are effective in activating immune cells.

The activating effect of the humanized antibodies of the present invention on CD4 T-cells was also measured. HuB9/HdB7, HuB10/HdB6 and HuB10/HdB7 can also prevent the conversion from AMP to adenosine, and thus reverse the left-shift level (83.5%, 83.7% and 83.4%, respectively). The aforesaid effect was similar to that of the 10H5 antibody. These results indicate that the humanized antibodies of the present invention can provide an activation effect on T-cells.

Example 8: Inhibitory Effect of the Antibodies of the Present Invention on the Tumor Growth in Mouse Model It is known that a nude mouse is a naturally mutated mouse that lacks T-cells. Thus, in the following experiments, the nude mouse was used as the model to test whether the antibodies of the present invention can inhibit tumor growth in vivo.

Researches have shown that the expression of CD73 will affect the tumorigenicity of MDA-MB-231 tumor cells (Clin Exp Metastasis (2007) 24:439-448; and Cancer Sci. 2010, vol. 101, 2561-2569). Therefore, MDA-MB-231 xenograft is the major animal model for testing the in vivo effects of an anti-CD73 antibody. In view of the above fact, the following experiment was carried to evaluate the in vivo activities of the antibodies of the present invention.

8-1. The Inhibitory Effect of the Antibodies of the Present Invention Against Tumor Growth in Mouse Model To investigate the inhibition of tumor growth by the 10H5 and its humanized derivatives, HuB9/HdB7, HuB10/HdB6 and HuB10/HdB7, Twenty-five Balb-C/Nu mice were used to build a xenograft model and then divided into 5 groups (5 mice/per group). MDA-MB-231 cells were injected into the mice, and when the tumor had grown to have a size of 170 mm³, the mice were injected with 10H5 and the three humanized antibodies, HuB9/HdB7, HuB10/HdB6 and HuB10/HdB7 30 mpk (mg/kg), twice a week (8 times in total).

The tumor size of mice in each group was observed 2 times a week. The results are shown in FIG. 7 and the following Table 1.

TABLE 1

| Group | TGI (%) |
|---|---|
| Vehicle (PBS) | 0.0 |
| 10H5 MM | 53.6 |
| HuB9/HdB7 | 41.1 |
| HuB10/HdB6 | 65.8 |
| HuB10/HdB7 | 49.5 |

Figure 7:
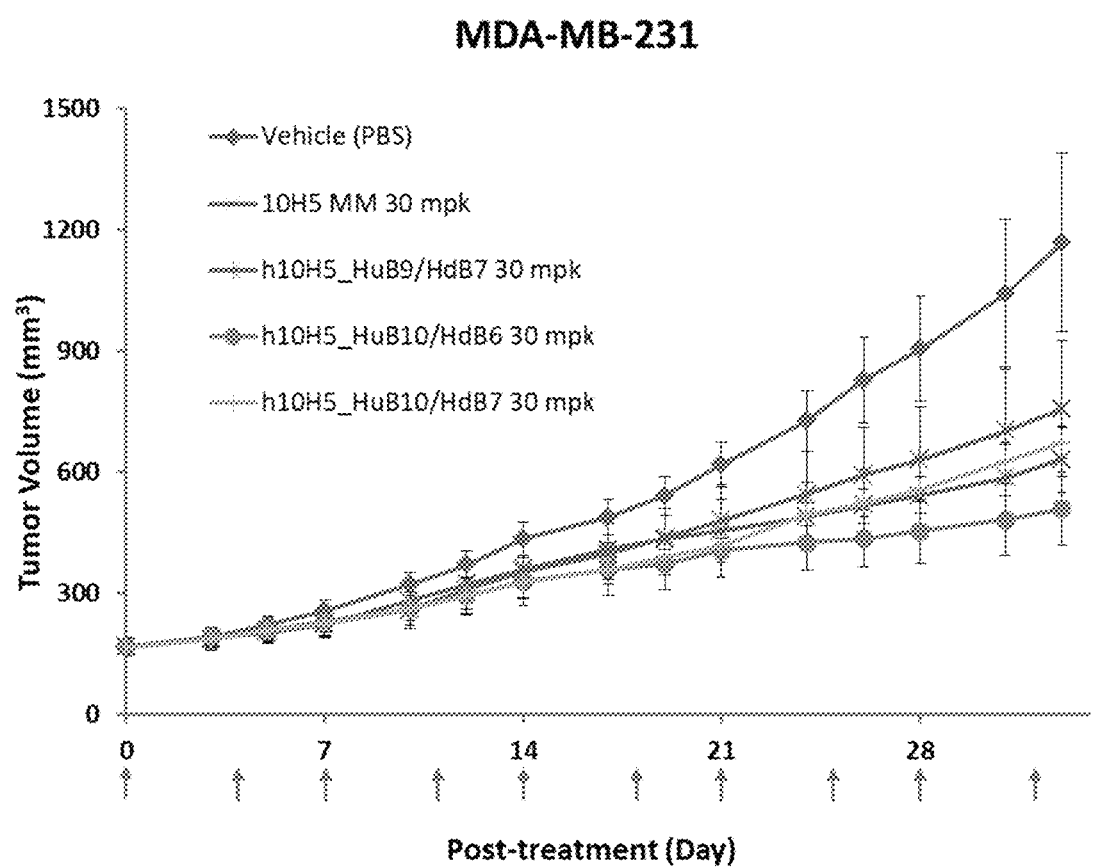
FIG. 7 indicates that the antibodies of the present invention, 10H5 and its humanized derivatives, HuB9/HdB7, HuB10/HdB6 and HuB10/HdB7, can inhibit MDA-MB-231 tumor growth in mouse xenograft model.

As shown in FIG. 7 and Table 1, as compared to the "Vehicle (PBS)" group, the growth of tumors in the 10H5, HuB9/HdB7, HuB10/HdB6 and HuB10/HdB7 treatments were all inhibited. The ratio of tumor growth inhibition (TGI) of the 10H5, HuB9/HdB7, HuB10/HdB6 and HuB10/HdB7 was 53.6%, 41.1%, 65.8%, and 49.5%, respectively. These results indicate that the 10H5 and its humanized derivatives all can inhibit the MDA-MB-231 tumor growth in Balb-C/Nu mice model.

8-2. The Inhibitory Effect of the Antibodies of the Present Invention Against the CD73 Activity in Tumor Tissues In order to further analyze that 10H5 antibodies actually have the ability to inhibit CD73 activity in tumor tissues, MDA-MB-231 cells formed tumors in Balb-C/Nu first, then different doses (3, 10 and 30 mpk) of 10H5 were injected into the tail vein of mice. The blood was collected 24 hours later, then sacrificed the animals to remove the tumors and to evaluate the CD73 activity in each tumor tissues. We analyzed the concentration of antibody in blood by MSD assays. The concentrations of 10H5 in the blood were presented as Table 2. The concentrations of 10H5 were exactly increased following the dose of the antibody administered (Table 2).

TABLE 2

| Group | Concentration (μg/ml) of antibody in blood after 24 h |
|---|---|
| 10H5 3 mpk | 14.4 ± 4.02 |
| 10H5 10 mpk | 36.3 ± 19.2 |
| 10H5 30 mpk | 58.0 ± 5.27 |

Figure 8:
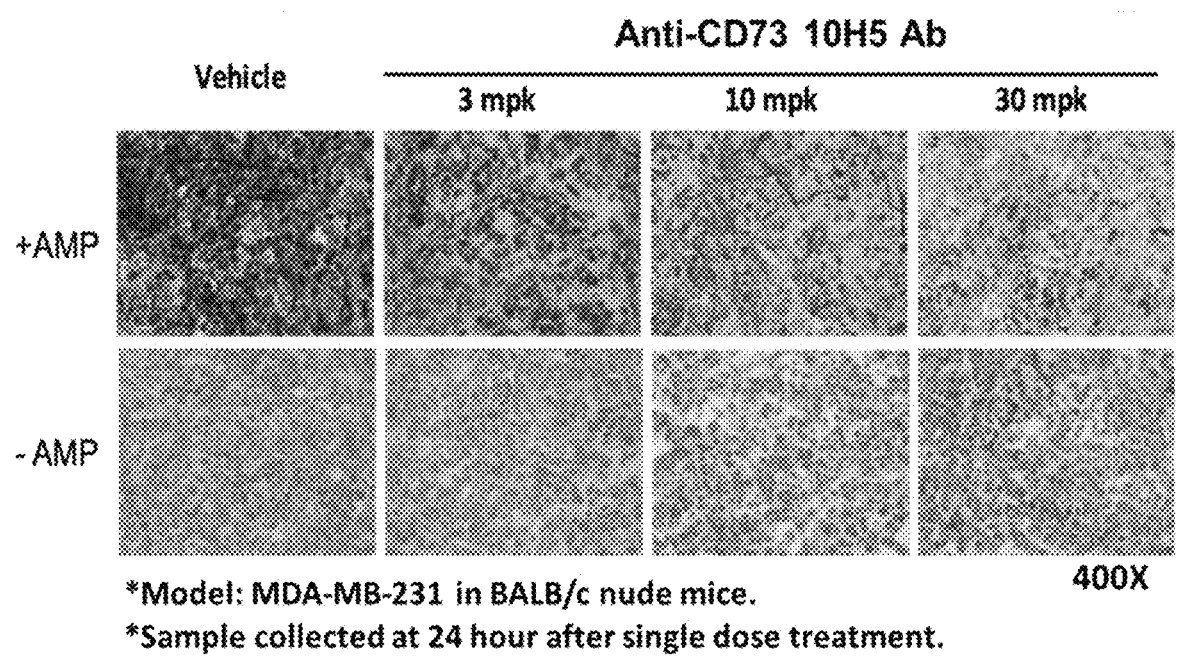
FIG. 8 shows the CD73 activity in tumor tissue was detected after the 24-hour treatment of the antibody of the present invention (e.g., 10H5), which was detected by in situ CD73 activity assay. The deep brown color indicates the presence of active CD73, whereas the light brown color indicates that CD73 enzymatic activity was inhibited by the increase dose of 10H5.

After the tumor tissue was cryosectioned, the tumor tissue was stained in situ by using the method by Mireia et al. (in situ CD73 activity assay: In Situ Identification of Ectoenzymes Involved in the Hydrolysis of Extracellular Nucleotides DOI: dx.doi.org/10.5772/intechopen.84495). The lighter of the staining, the more CD73 activity is inhibited by the antibody. As shown in FIG. 8, the tissue of tumors with vehicle treatment, the result of the staining is deep brown. However, the staining of tumors was gradually turning to light brown following the increase doses of 10H5 treatment. The phenomenon of dose-dependent in situ CD73 inhibition were also observed in humanized antibodies.

Example 9: Epitope Mapping

To investigate the epitope of the antibody of the present invention, the following experiments were conducted.

Figure 9:
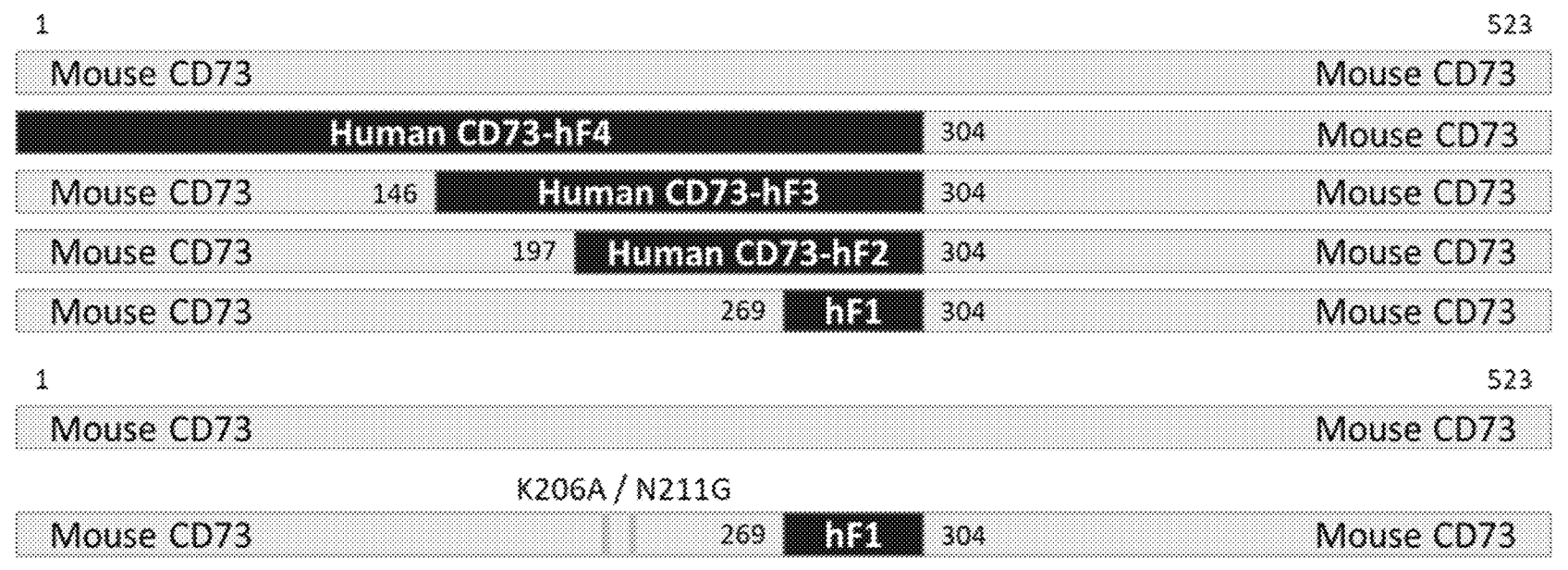

Five mouse-human domain swapping proteins were constructed. As shown in FIG. 9, the five proteins have sequences as follows:

1. mCD73hF4: mouse CD73 with 1-304 swapped to the amino acid sequence of human CD73;
2. mCD73hF3: mouse CD73 with 146-304 swapped to the amino acid sequence of human CD73;
3. mCD73hF2: mouse CD73 with 197-304 swapped to the amino acid sequence of human CD73;
4. mCD73hF1: mouse CD73 with 269-304 swapped to the amino acid sequence of human CD73; and
5. mCD73hF1-K206A-N211G: not only mouse CD73 with 269-304 swapped to the amino acid sequence of human CD73, but also the lysine residue at position 206 and asparagine residue at position 211 were substituted with alanine and glycine, respectively The above five mouse-human domain swapping proteins and mouse CD73 were individually cloned into F293 cells to express. By using ELISA assay, those proteins were then be analyzed the binding affinity of anti-CD73 antibodies (e.g., Oleclumab and 10H5). The results are shown in FIG. 10.

Figure 10:
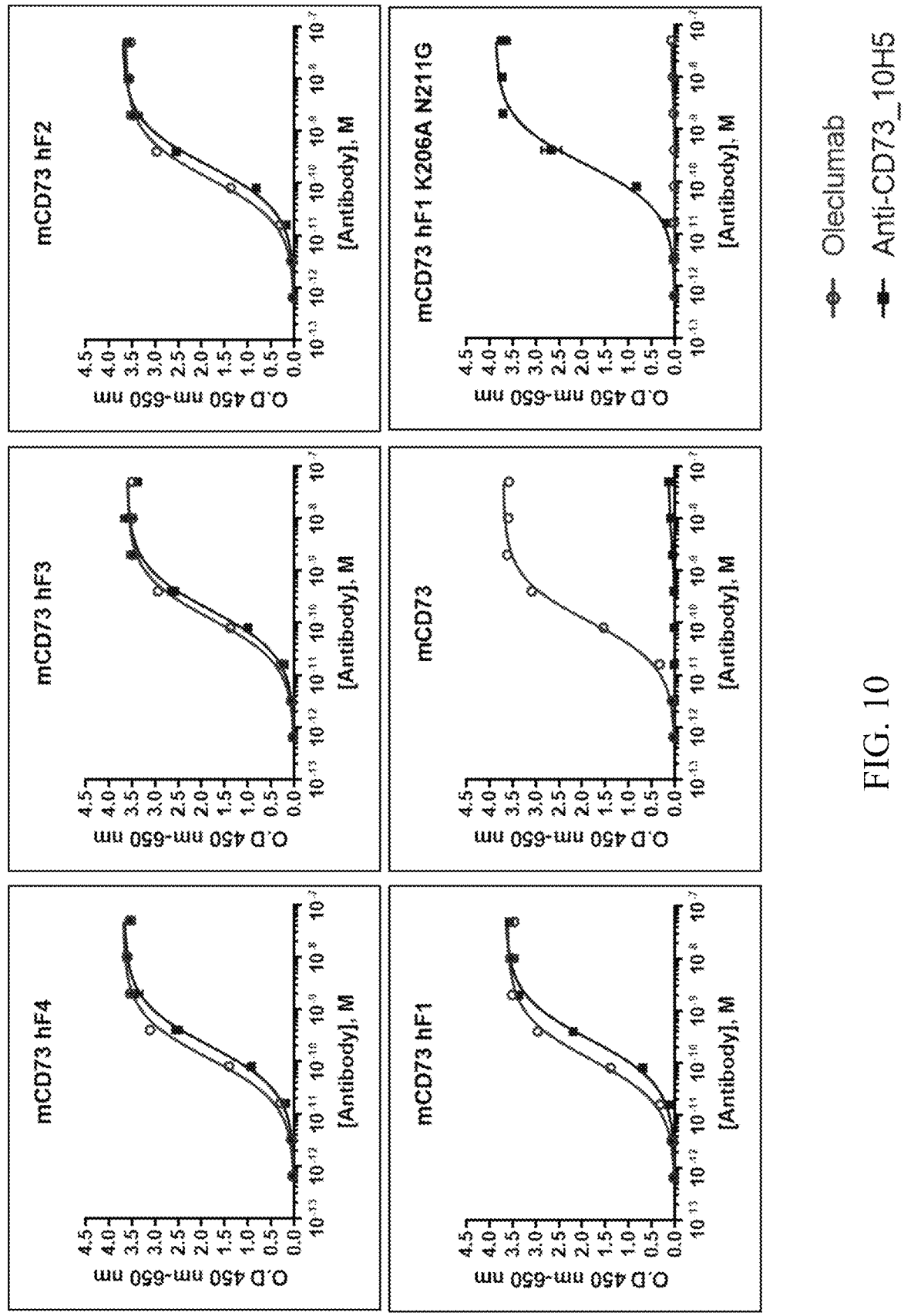
FIG. 10 indicates that 10H5 has species specificity and binds to the human CD73 on the amino acids at positions 269-304, which is different from the binding sites of Oleclumab (i.e., K206 and N211).

As shown in FIG. 10, Oleclumab can bind to mouse CD73 and mCD73hF1 to mCD73hF4, while cannot bind to mCD73hF1-K206A-N211G (the loss of this mutant binding to MEDI9447 has been disclosed in U.S. Pat. No. 9,938, 356B2). That is, Oleclumab can binds to both mouse CD73 and human CD73 on the lysine residue at position 206 and asparagine residue at position 211. On the other hand, 10H5 can bind to mCD73hF1 to mCD73hF4 and mCD73hF1-K206A-N211G, while cannot bind to mouse CD73. These results indicate that 10H5 has species specificity and binds to the CD73 on the amino acids at positions 269-304. It also shows that 10H5 is different from Oleclumab by the binding site at 269 to 304 which is different from the K206 and N211 recognized by Oleclumab.

Figure 11:
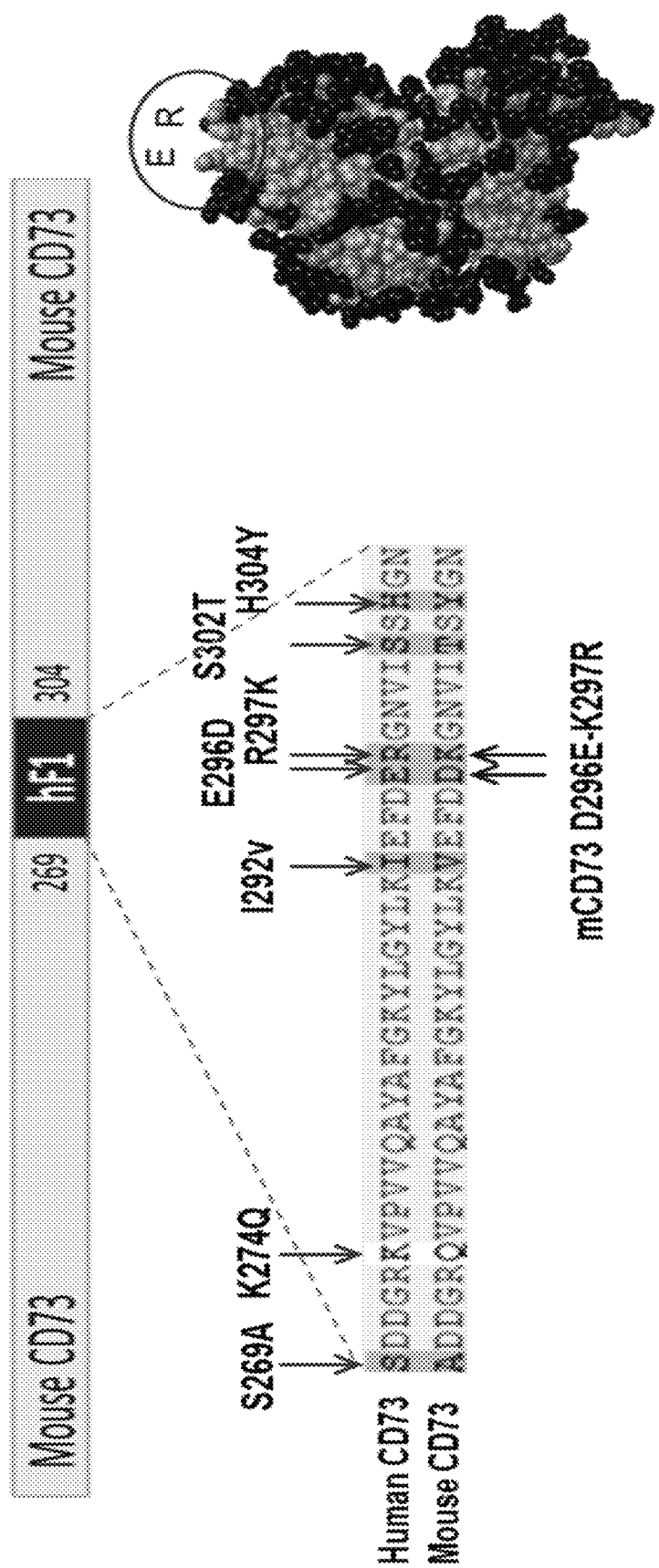
FIG. 11 shows the amino acid residue at positions that are different between mouse CD73 and human CD73, and can be mutated for mapping the binding positions of the antibodies of the present invention.

To further clarify the position 269 to 304 of CD73 being bound by 10H5 antibody, the amino acid residue at positions 269, 274, 292, 296, 297, 302, and 304, which are different between human CD73 and mouse CD73, were mutated individually to check the binding epitope of the 10H5 antibody. Thus, mCD73hF1 was made further mutations on the above positions to construct the following eight proteins: mCD73hF1-S269A, mCD73hF1-K274Q, mCD73hF1-I292V, mCD73hF1-E296D, mCD73hF1-R297K, mCD73hF1-S302T, mCD73hF1-H304Y and mCD73hF1-E296D-R297K. The positions of the mutation sites are shown in FIG. 11.

The above eight proteins and mCD73hF1 were respectively cloned into F293 cells to express, and then the binding affinity between 10H5 antibody and those proteins was analyzed by using ELISA. The results are shown in FIG. 12.

Figure 12:
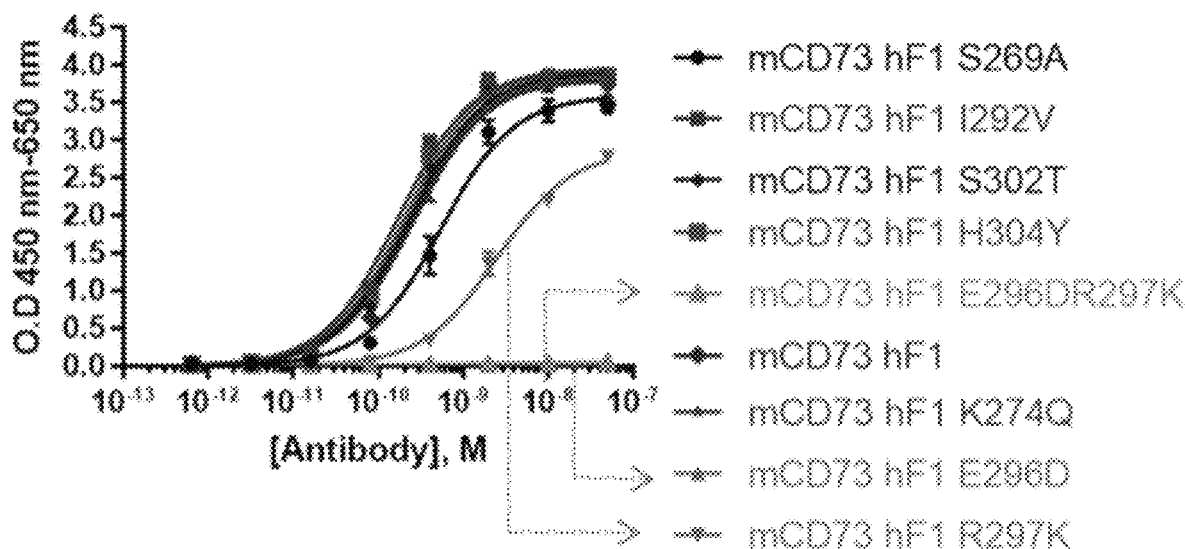
FIG. 12 indicates that the antibodies of the present invention (e.g., 10H5) bind to the CD73 depending on the glutamic acid residue at position 296 and the arginine residue at position 297.

As shown in FIG. 12 10H5 can completely binds to mCD73hF1, mCD73hF1-S269A, mCD73hF1-K274Q, mCD73hF1-I292V, mCD73hF1-S302T, and mCD73hF1-H304Y, but the binding affinity to mCD73hF1-R297K ($KD=2.49\times10^{-9}$) was only about one tenth of that to mCD73hF1 ($KD=2.54\times10^{-10}$). When the glutamic acid residue at position 296 was mutated (i.e., mCD73hF1-E296D and mCD73hF1-E296D-R297K), the binding affinity between 10H5 antibody and CD73 would disappear.

These results indicate that the antibodies of the present invention (e.g., 10H5) bind to the CD73 dependent on glutamic acid residue at position 296 and the arginine residue at position 297.

Figure 13:
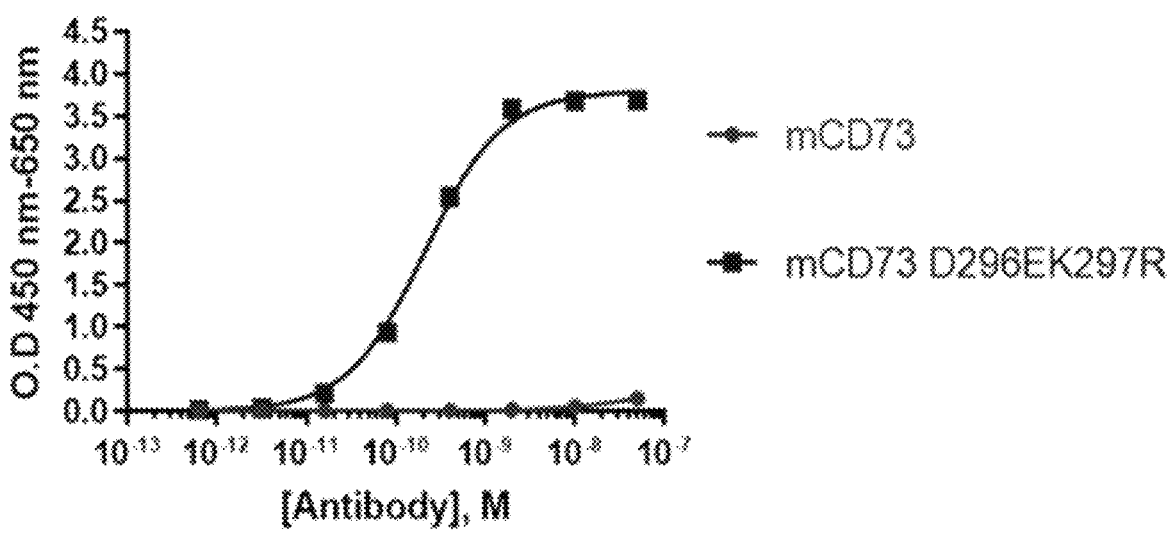
FIG. 13 shows the ELISA results, representing the binding affinity of the antibodies of the present invention to mouse CD73-D296E-K297R, to confirm that the antibodies of the present invention (e.g., 10H5) bind to the CD73 depending on the glutamic acid residue at position 296 and the arginine residue at position 297.

Furthermore, two mutations were introduced into mouse CD73, wherein the aspartate residue at position 296 was substituted with glutamic acid residue and the lysine residue at position 297 was substituted with arginine residue (hereinafter referred to as "mouse CD73-D296E-K297R") (FIG. 13). The binding affinity of 10H5 between mouse CD73 and mouse CD73-D296EK297R was analyzed by using ELISA. The results are shown in FIG. 13

As shown in FIG. 13, 10H5 antibody cannot bind to mouse CD73, while can bind to mouse CD73-D296EK297R. These results indicate again that the antibodies of the present invention (e.g., 10H5) bind to the CD73 dependent on glutamic acid residue at position 296 and the arginine residue at position 297.

Example 10: Mapping the Binding Positions of Antibodies of the Present Invention to CD73

Figure 14A:
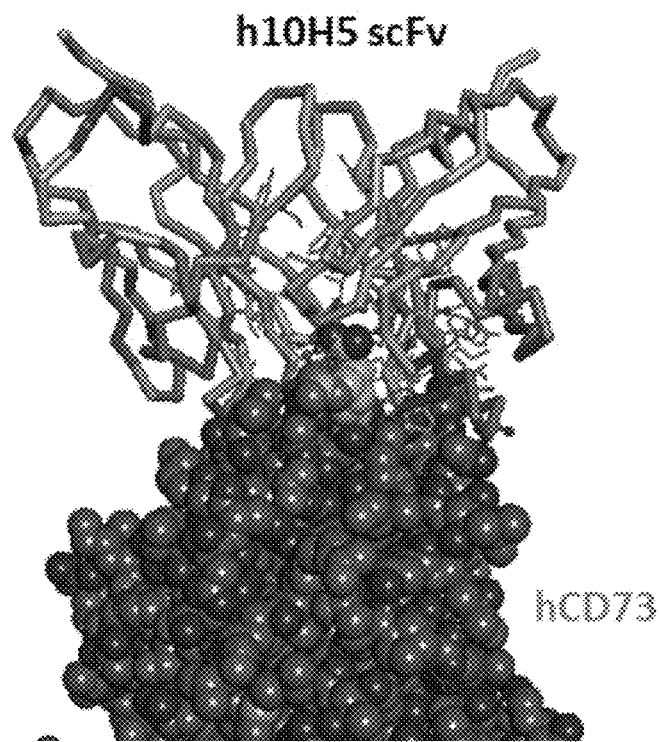
FIG. 14A shows a 3D structure model, simulating the interactions between human CD73 and 10H5 scFv antibody.

10-1. 3D Structure Model Simulation of the Interactions Between CD73 and 10H5 scFv Antibody To identify the amino acids on the 10H5 antibody that involves in its interaction with E296/R297 of human CD73 antigen, 3D structure model simulation and logical intelligence analysis were used (FIG. 14A).

Figure 14B:
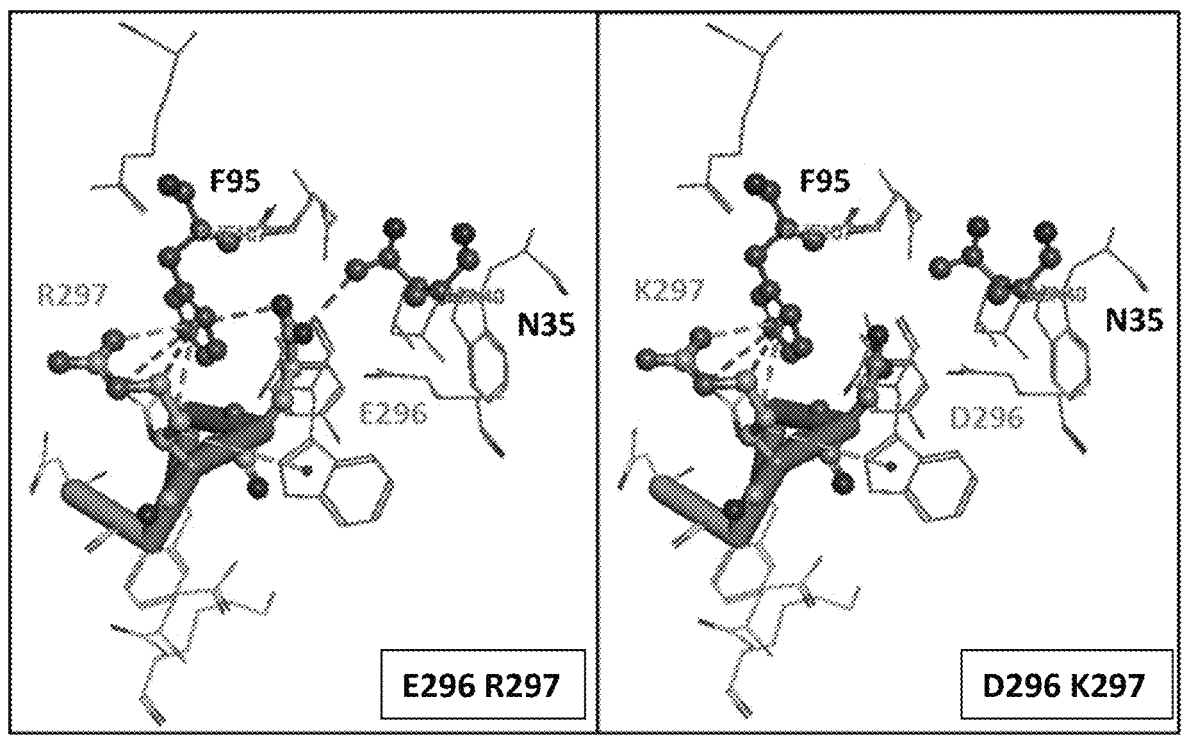
FIG. 14B shows that 10H5 scFv antibody binds to the human CD73 on glutamic acid residue at position 296 and the arginine residue at position 297.
Figure 14C:
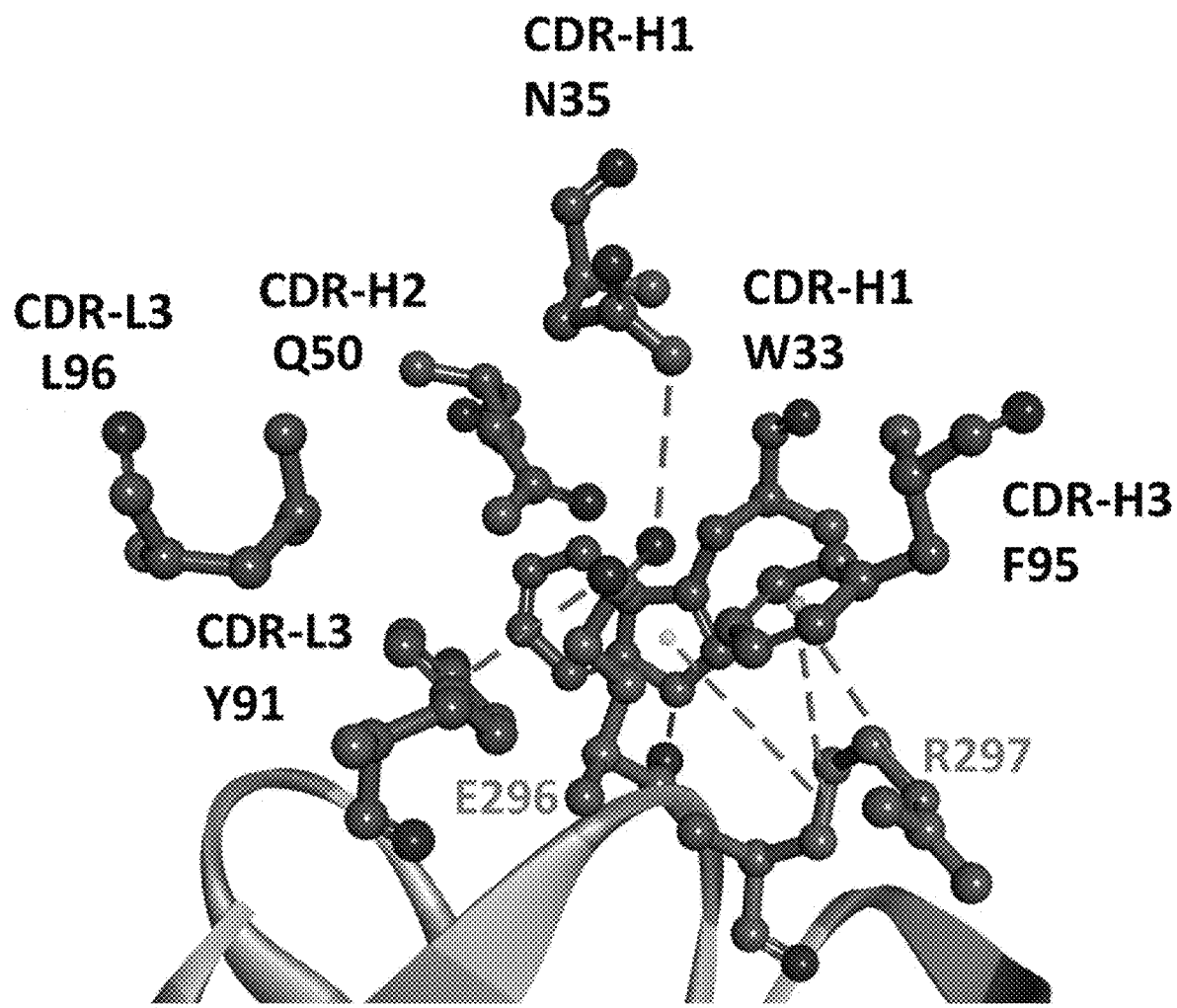
FIG. 14C shows that there are hydrogen bonds, hydrophobic effect, and ion-ion interaction between the six amino acids (W33 of CDR-H1, N35 of CDR-H1, Q50 of CDR-H2, F95 of CDR-H3, Y91 of CDR-L3 and L96 of CDR-L3) of 10H5 scFv antibody and human CD73 (on glutamic acid residue at position 296 and the arginine residue at position 297).

As shown in FIG. 14B, 10H5 scFv antibody binds to the CD73 on glutamic acid residue at position 296 and the arginine residue at position 297, and if the residues at these two positions were respectively mutated to be aspartic acid and lysine, the binding between 10H5 scFv antibody and CD73 disappeared. According to FIGS. 14A and 14B, E296/R297 of human CD73 might be surrounded by four loops of 10H5 antibody (i.e., CDR-H1, CDR-H2, CDR-H3, and CDR-L3), and potential six amino acids (W33 of CDR-H1, N35 of CDR-H1, Q50 of CDR-H2, F95 of CDR-H3, Y91 of CDR-L3 and L96 of CDR-L3) on the antibody that can generate hydrogen bond, hydrophobic effect and ion-ion interaction with CD73 (FIG. 14C).

10-2. Binding Positions Mapping

To investigate the binding positions of the antibody of the present invention and confirm the prediction of the 3D model as described above, the following experiments were conducted.

To prove the prediction of the 3D model as described above is true, the four mutated antibodies were constructed and expressed, including 10H5-CDRH1N35A, 10H5-CDRH3F95A, 10H5-CDRH1W33A and 10H5-CDRL3Y91A, to examine whether these antibodies will be loss of function. The binding affinities of the above four mutated antibodies, 10H5 antibody, Oleclumab, and IgG to mouse CD73 and mouse CD73 hF1 were respectively analyzed by using ELISA assay. The results are shown in FIG. 15.

Figure 15:
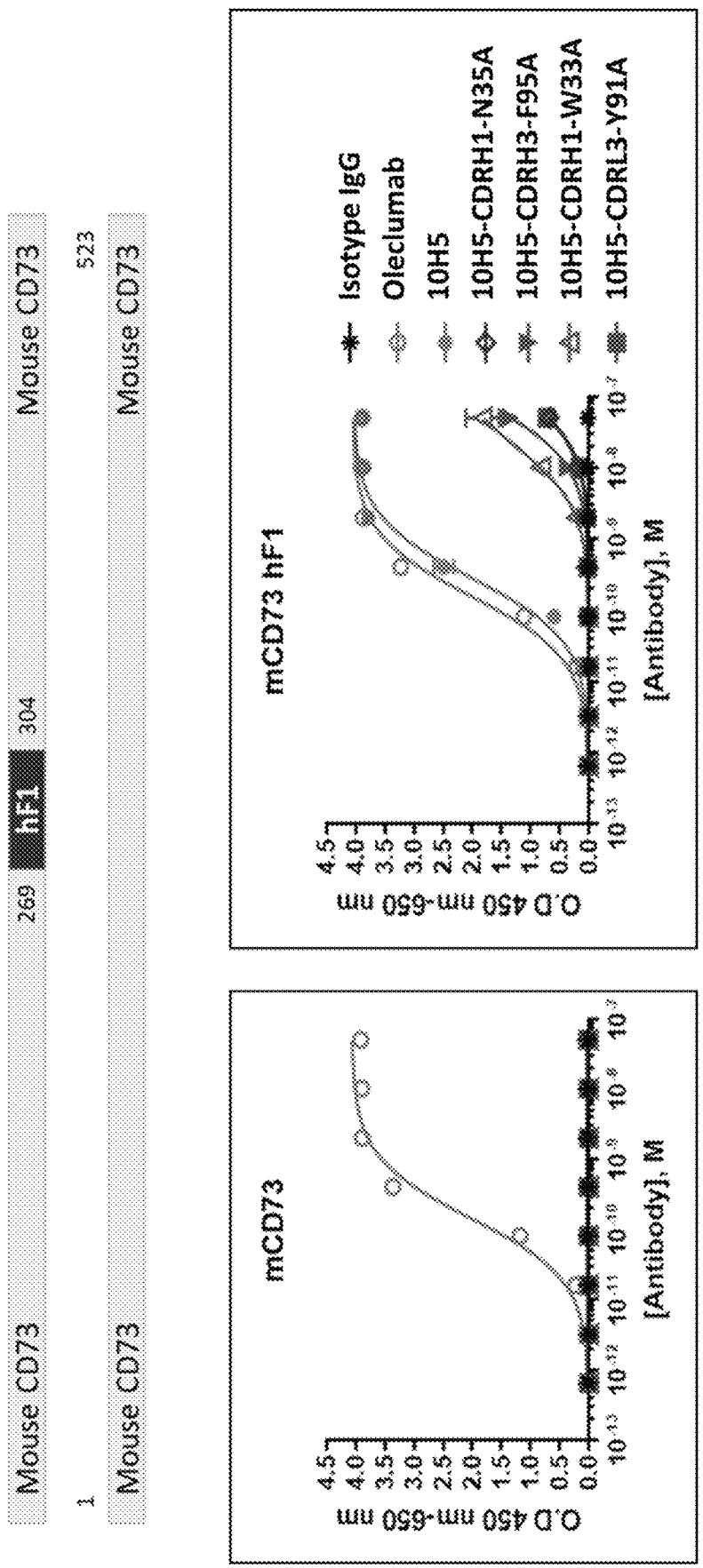
FIG. 15 shows that 4 positions: W33 of CDR-H1, N35 of CDR-H1, F95 of CDR-H3, and Y91 of CDR-L3 of 10H5 antibody were respectively mutated to alanine for mapping the binding positions of the antibodies of the present invention, wherein the results show that 10H5 could not bind to the mouse CD73 (left figure), but could bind to the mouse CD73 containing hF1 (human CD73 residues 269-304) (right figure). However, all of the four mutated antibodies could not bind to mouse CD73 hF1 (right figure). These results confirm that the 3D structure model can simulate the interactions between CD73 and 10H5 antibody.

As shown in FIG. 15, Oleclumab can bind to mouse CD73 and mCD73hF1, while 10H5 can only bind to mCD73hF1. On the other hand, 10H5-CDRH1N35A, 10H5-CDRH3F95A, 10H5-CDRH1W33A, and 10H5-CDRL3Y91A cannot bind to both the mouse CD73 and mCD73hF1. These results indicate that the W33 of CDR-H1, N35 of CDR-H1, F95 of CDR-H3, and Y91 of CDR-L3 are indeed involved in the binding of the antibody of the present invention (e.g., 10H5) to human CD73. That is, the 3D structure model established in Example 15-1 is correct. W33 of CDR-H1, N35 of CDR-H1, Q50 of CDR-H2, F95 of CDR-H3, Y91 of CDR-L3, and L96 of CDR-L3 are the key binding positions on 10H5 antibody.

10-3. Screening and Selecting Antibodies that have Similar Epitope as 10H5

To screen more antibodies that (i) can bind to human CD73 (E296/R297) at the same amino acids as 10H5 antibody, and (ii) can inhibit the activity of CD73, the six amino acids (i.e., W33 of CDR-H1, N35 of CDR-H1, Q50 of CDR-H2, F95 of CDR-H3, Y91 of CDR-L3 and L96 of CDR-L3) were randomly mutated to construct a single-chain phage display library. Sixteen phage clones (i.e., 109A03, 110A06, 110B03, 111B03, 111D04, 112A05, 112B02, 113D04, 114B07, 114C01, 114C12, 114D07, 114E08, 114G05, 116C07, 116G02) were selected out by binding to the mouse CD73 antigen with D296E-K297R mutation and the heavy chain and the light chain variable domains were constructed into full-length IgG4 antibodies. The mutation position and the sequence ID No. of the variable domain either in heavy chain or in light chain of the 16 phage clones are shown in FIG. 16. The binding affinities ($K_D$) of the aforesaid 16 antibodies to mouse CD73 with D296E-K297R mutation were respectively analyzed by ELISA and were shown in FIG. 16.

10-4. Inhibitory Effect of Antibodies, which Selected from the Library Constructed According to the 3D Model, on the CD73 Activity In this experiment, the detection of the inhibitory effect on CD73 activity method was the same as Example 1 by using MDA-MB-231 cancer cells, except that (i) the concentration of antibodies was 10 nM, and (ii) the concentration of AMP was 100 μM. Luminometer was used for measuring the luminescence of each group after the cells of each group were incubated for 6 hours and 24 hours. The results were shown in FIG. 17A (109A03, 110A06, 110B03, 111B03, 111D04, 112A05, 112B02, 113D04,) and FIG. 17B (114B07, 114C01, 114C12, 114D07, 114E08, 114G05, 116C07, 116G02).

Figure 17A:
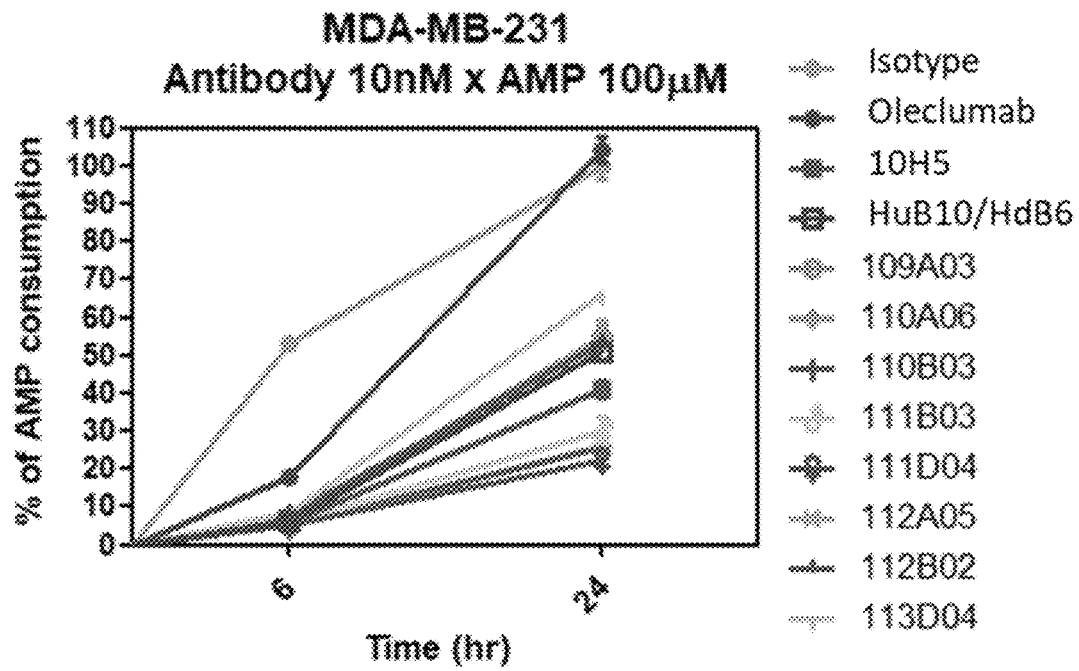
FIGS. 17A and 17B indicate that all the 16 antibodies selected from the phage display library and were constructed into hIgG4 type, as well as the 10H5 antibody and its humanized derivatives (i.e., HuB10/HdB6), can inhibit the CD73 activity of MDA-MB-231 cells.
Figure 17B:
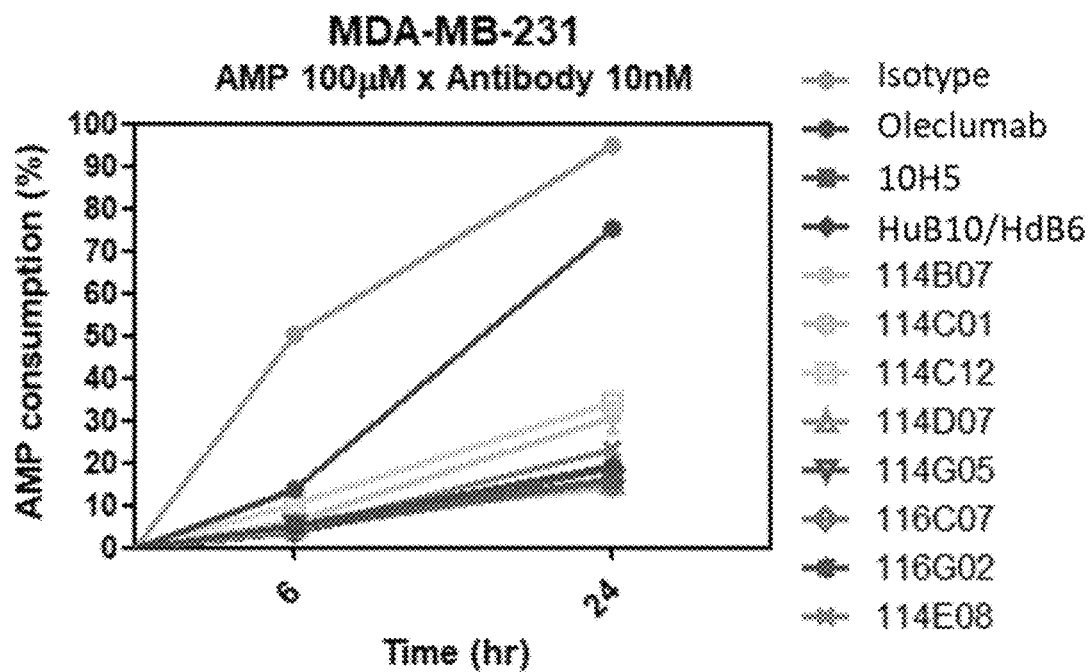

As shown in FIGS. 17A and 17B, after 6 hours of culturing, both the "Oleclumab" and the antibodies of the present invention (i.e., 109A03, 110A06, 110B03, 111B03, 111D04, 112A05, 112B02, 113D04, 114B07, 114C01, 114C12, 114D07, 114E08, 114G05, 116C07, 116G02) can inhibit the consumption of AMP, wherein the antibodies of the present inventions have a better inhibitory effect than Oleclumab. On the other hand, after 24 hours of culturing, the "Oleclumab" cannot inhibit the consumption of AMP. However, the antibodies of the present inventions (i.e., 109A03, 110A06, 110B03, 111B03, 111D04, 112A05, 112B02, 113D04, 114B07, 114C01, 114C12, 114D07, 114E08, 114G05, 116C07, 116G02) can still significantly inhibit the consumption of AMP. These results indicate that, as compared to the Oleclumab, the antibodies of the present invention have a better and longer inhibitory effect on CD73 activity on MDA-MB-231 cancer cells.

The invention claimed is:

1. An antibody or antigen-binding fragment thereof comprising:
   a heavy chain variable domain comprising a HCDR1 region, a HCDR2 region and a HCDR3 region, wherein the HCDR1 region comprises the amino acid sequence of SEQ ID NO: 4; the HCDR2 region comprises the amino acid sequence of SEQ ID NO: 5; and the HCDR3 region comprises the amino acid sequence of SEQ ID NO: 6; and
   a light chain variable domain comprising a LCDR1 region, a LCDR2 region and a LCDR3 region, wherein the LCDR1 region comprises the amino acid sequence of SEQ ID NO: 7, the LCDR2 region comprises the amino acid sequence of SEQ ID NO: 8, and the LCDR3 region comprises the amino acid sequence of SEQ ID NO: 9 or the amino acid sequence of SEQ ID NO: 9 with substitution of leucine residue at position 8 by methionine, glycine, histidine, arginine, glutamine or isoleucine, wherein the antibody or antigen-binding fragment thereof binds to CD73 on at least one of the glutamic acid residue at position 296 and the arginine residue at position 297.

2. The antibody or antigen-binding fragment thereof according to claim 1, wherein:
the LCDR1 region comprises the amino acid sequence of SEQ ID NO: 7;
the LCDR2 region comprises the amino acid sequence of SEQ ID NO: 8; and
the LCDR3 region comprises the amino acid of SEQ ID NO: 9.

3. The antibody or antigen-binding fragment thereof according to claim 1, wherein the light chain variable domain comprises the amino acid sequence selected from the group consisting of SEQ ID NO: 3, SEQ ID NO: 12, SEQ ID NO: 13 and SEQ ID NO: 39 to SEQ ID NO:44.

4. The antibody or antigen-binding fragment thereof according to claim 1, further comprises one or more of (1) a linker peptide between the heavy chain variable domain and the light chain variable domain, (2) a heavy chain constant region, (3) a light chain constant region, and (4) an Fc region.

5. The antibody or antigen-binding fragment thereof according to claim 1, which is a single chain antibody fragment, a bispecific antibody, a single-domain antibody, a nanobody, a chimeric antibody, or a partially or fully humanized antibody.

6. The antibody or antigen-binding fragment thereof according to claim 1, which further links with a drug conjugate to form an antibody-drug conjugate (ADC), or further links with a second antibody or a second antigen-binding fragment to form a bispecific antibody.

7. The antibody or antigen-binding fragment thereof according to claim 1, which further comprises a fragment derived from IgG1, IgG2, IgG3 or IgG4.

8. A pharmaceutical composition comprising (i) an antibody or antigen-binding fragment thereof according to claim 1, a nucleic acid molecule encoding the aforesaid antibody or antigen-binding fragment thereof, a vector comprising the aforesaid nucleic acid molecule, a recombinant host cell comprising the aforesaid nucleic acid molecule, or a recombinant host cell comprising the aforesaid vector, and (ii) a pharmaceutically acceptable carrier.

9. The pharmaceutical composition according to claim 8, which is used for inhibiting CD73.

10. The pharmaceutical composition according to claim 8, which further comprises one or more other immunotherapy agents.

11. The pharmaceutical composition according to claim 10, wherein the other immunotherapy agent is PD-1 antagonist, PD-L1 antagonist or CTLA-4 antagonist.

12. The pharmaceutical composition according to claim 8, is used for activating T-cells, activating B-cells, activating NK cells and/or inhibiting cancer cells.

13. The pharmaceutical composition according to claim 8, which is used for treating and/or ameliorating cancer.

14. The pharmaceutical composition according to claim 13, wherein the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma and lymphoma.

15. An antibody or antigen-binding fragment thereof, comprising:
a heavy chain variable domain comprising the amino acid sequence selected from the group consisting of SEQ ID NO: 2, SEQ ID NO: 10, SEQ ID NO: 11 and SEQ ID NO: 29 to SEQ ID NO: 38; and
a light chain variable domain comprising a LCDR1 region, a LCDR2 region and a LCDR3 region, wherein the LCDR1 region comprises the amino acid sequence of SEQ ID NO: 7, the LCDR2 region comprises the amino acid sequence of SEQ ID NO: 8, and the LCDR3 region comprises the amino acid sequence of SEQ ID NO: 9 or the amino acid sequence of SEQ ID NO: 9 with substitution of leucine residue at position 8 by methionine, glycine, histidine, arginine, glutamine or isoleucine,
wherein the antibody or antigen-binding fragment thereof binds to CD73 on at least one of the glutamic acid residue at position 296 and the arginine residue at position 297.

16. The antibody or antigen-binding fragment thereof according to claim 15, wherein the light chain variable domain comprises the amino acid sequence selected from the group consisting of SEQ ID NO: 3, SEQ ID NO: 12, SEQ ID NO: 13 and SEQ ID NO: 39 to SEQ ID NO:44.

17. The antibody or antigen-binding fragment thereof according to claim 15, which further comprises one or more of (1) a linker peptide between the heavy chain variable domain and the light chain variable domain, (2) a heavy chain constant region, (3) a light chain constant region, and (4) an Fc region.

18. The antibody or antigen-binding fragment thereof according to claim 15, is a single chain antibody fragment, a bispecific antibody, a single-domain antibody, a nanobody, a chimeric antibody, or a partially or fully humanized antibody.

19. The antibody or antigen-binding fragment thereof according to claim 15, which further links with a drug conjugate to form an antibody-drug conjugate (ADC), or further links with a second antibody or a second antigen-binding fragment to form a bispecific antibody.

20. The antibody or antigen-binding fragment thereof according to claim 15, which further comprises a fragment derived from IgG1, IgG2, IgG3 or IgG4.

21. A pharmaceutical composition comprising (i) an antibody or antigen-binding fragment thereof according to claim 15, nucleic acid molecule encoding the aforesaid antibody or antigen-binding fragment thereof, a vector comprising the aforesaid nucleic acid molecule, a recombinant host cell comprising the aforesaid nucleic acid molecule, or a recombinant host cell comprising the aforesaid vector, and (ii) a pharmaceutically acceptable carrier.

22. The pharmaceutical composition according to claim 21, which is used for inhibiting CD73.

23. The pharmaceutical composition according to claim 21, which further comprises one or more other immunotherapy agents.

24. The pharmaceutical composition according to claim 23, wherein the other immunotherapy agent is PD-1 antagonist, PD-L1 antagonist or CTLA-4 antagonist.

25. The pharmaceutical composition according to claim 21, which is used for activating T-cells, activating B-cells, activating NK cells and/or inhibiting cancer cells.

26. The pharmaceutical composition according to claim 21, which is used for treating and/or ameliorating cancer.

27. The pharmaceutical composition according to claim 26, wherein the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma and lymphoma.

28. A method of inhibiting CD73, comprising administering a subject an effective amount of an antibody or antigen-binding fragment thereof according to claim 1 or 15 or a pharmaceutical composition according to claim 8.

29. The method according to claim 28, wherein the method further comprises administering one or more other immunotherapy agents to the subject.

30. The method according to claim 29, wherein the other immunotherapy agent is PD-1 antagonist, PD-L1 antagonist or CTLA-4 antagonist.

31. The method according to claim 28, which is for activating T-cells, activating B-cells, activating NK cells and/or inhibiting cancer cells.

32. The method according to claim 28, which is for treating and/or ameliorating cancer.

33. The method according to claim 32, wherein the cancer is selected from the group consisting of breast cancer, gastric cancer, colorectal cancer, gallbladder cancer, prostate cancer, ovarian carcinoma, chronic or acute lymphocytic leukemia, bladder cancer, brain tumor, kidney carcinoma, head and neck squamous cell carcinoma, glioblastoma, esophageal cancer, pancreatic cancer, renal carcinoma, oral cancer, lung cancer, colon adenocarcinoma, melanoma and lymphoma.

* * * * *

SEQUENCE LISTING

<160> NUMBER OF SEQ ID NOS: 44

<210> SEQ ID NO 1
<211> LENGTH: 555
<212> TYPE: PRT
<213> ORGANISM: Homo sapiens

<400> SEQUENCE: 1

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
            195                 200                 205

Thr Leu Asn Val Asn Lys Ile Ile Ala Leu Gly His Ser Gly Phe Glu
    210                 215                 220
```

```
Met Asp Lys Leu Ile Ala Gln Lys Val Arg Gly Val Asp Val Val
225                 230                 235                 240

Gly Gly His Ser Asn Thr Phe Leu Tyr Thr Gly Asn Pro Pro Ser Lys
            245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
            275                 280                 285

Tyr Leu Lys Ile Glu Phe Asp Glu Arg Gly Asn Val Ile Ser Ser His
290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
            325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
            355                 360                 365

Ile Asn Asn Asn Leu Arg His Ala Asp Glu Thr Phe Trp Asn His Val
370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
530                 535                 540

Arg Ile Lys Phe Ser His His His His His
545                 550                 555

<210> SEQ ID NO 2
<211> LENGTH: 112
<212> TYPE: PRT
<213> ORGANISM: Mus musculus

<400> SEQUENCE: 2

Gln Val Lys Leu Gln Gln Ser Gly Ala Glu Leu Val Lys Pro Gly Ala
1               5                   10                  15

Ser Val Lys Ile Ser Cys Lys Ala Ser Gly Tyr Val Phe Ser Ser Tyr
            20                  25                  30

Trp Ile Asn Trp Val Lys Gln Arg Pro Gly Lys Gly Leu Glu Trp Ile
```

```
                35                  40                  45
Gly Gln Ile Tyr Pro Gly Asp Gly Asn Thr Asn Tyr Asn Arg Asn Phe
 50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Gly Phe Ala Asp Trp Gly Gln Gly Thr Thr Val Thr Val Ser Ser
            100                 105                 110
```

<210> SEQ ID NO 3
<211> LENGTH: 107
<212> TYPE: PRT
<213> ORGANISM: Mus musculus

<400> SEQUENCE: 3

```
Asp Ile Glu Leu Thr Gln Ser Pro Ser Ser Leu Ser Ala Ser Leu Gly
 1               5                  10                  15

Glu Arg Val Ser Leu Thr Cys Arg Ala Ser Gln Asp Ile Gly Asp Ser
                 20                  25                  30

Leu Ile Trp Leu Gln Gln Glu Pro Asp Gly Thr Ile Lys Arg Leu Ile
             35                  40                  45

Tyr Ala Thr Ser Ser Leu Asp Ser Gly Val Pro Lys Arg Phe Ser Gly
 50                  55                  60

Ser Arg Ser Gly Thr Lys Tyr Ser Leu Thr Ile Ser Ser Val Glu Ala
 65                  70                  75                  80

Glu Asp Ala Ala Thr Tyr Tyr Cys Gln Gln Tyr Ser Gly Tyr Pro Leu
                 85                  90                  95

Thr Phe Gly Ser Gly Thr Lys Leu Glu Ile Lys
            100                 105
```

<210> SEQ ID NO 4
<211> LENGTH: 10
<212> TYPE: PRT
<213> ORGANISM: Mus musculus

<400> SEQUENCE: 4

```
Gly Tyr Val Phe Ser Ser Tyr Trp Ile Asn
 1               5                  10
```

<210> SEQ ID NO 5
<211> LENGTH: 17
<212> TYPE: PRT
<213> ORGANISM: Mus musculus

<400> SEQUENCE: 5

```
Gln Ile Tyr Pro Gly Asp Gly Asn Thr Asn Tyr Asn Arg Asn Phe Lys
 1               5                  10                  15

Gly
```

<210> SEQ ID NO 6
<211> LENGTH: 3
<212> TYPE: PRT
<213> ORGANISM: Mus musculus

<400> SEQUENCE: 6

```
Phe Ala Asp
 1
```

```
<210> SEQ ID NO 7
<211> LENGTH: 11
<212> TYPE: PRT
<213> ORGANISM: Mus musculus

<400> SEQUENCE: 7

Arg Ala Ser Gln Asp Ile Gly Asp Ser Leu Ile
1               5                   10

<210> SEQ ID NO 8
<211> LENGTH: 7
<212> TYPE: PRT
<213> ORGANISM: Mus musculus

<400> SEQUENCE: 8

Ala Thr Ser Ser Leu Asp Ser
1               5

<210> SEQ ID NO 9
<211> LENGTH: 9
<212> TYPE: PRT
<213> ORGANISM: Mus musculus

<400> SEQUENCE: 9

Gln Gln Tyr Ser Gly Tyr Pro Leu Thr
1               5

<210> SEQ ID NO 10
<211> LENGTH: 112
<212> TYPE: PRT
<213> ORGANISM: Artificial Sequence
<220> FEATURE:
<223> OTHER INFORMATION: Humanized antibody

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Ser Tyr
                20                  25                  30

Trp Ile Asn Trp Val Arg Gln Ala Pro Gly Gln Gly Leu Glu Trp Met
            35                  40                  45

Gly Gln Ile Tyr Pro Gly Asp Gly Asn Thr Asn Tyr Asn Arg Asn Phe
        50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Gly Phe Ala Asp Trp Gly Gln Gly Thr Leu Val Thr Val Ser Ser
                100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Humanized antibody

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Ser Tyr
                20                  25                  30
```

```
Trp Ile Asn Trp Val Arg Gln Ala Pro Gly Gln Gly Leu Glu Trp Met
            35                  40                  45

Gly Gln Ile Tyr Pro Gly Asp Gly Asn Thr Asn Tyr Asn Arg Asn Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Phe Ala Asp Trp Gly Gln Gly Thr Leu Val Thr Val Ser Ser
                100                 105                 110

<210> SEQ ID NO 12
<211> LENGTH: 107
<212> TYPE: PRT
<213> ORGANISM: Artificial Sequence
<220> FEATURE:
<223> OTHER INFORMATION: Humanized antibody

<400> SEQUENCE: 12

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asp Ser
                 20                  25                  30

Leu Ile Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
 50                  55                  60

Ser Arg Ser Gly Thr Asp Tyr Thr Leu Thr Ile Ser Ser Val Gln Pro
 65                  70                  75                  80

Glu Asp Phe Ala Thr Tyr Tyr Cys Gln Gln Tyr Ser Gly Tyr Pro Leu
                 85                  90                  95

Thr Phe Gly Gln Gly Thr Lys Val Glu Ile Lys
                100                 105

<210> SEQ ID NO 13
<211> LENGTH: 107
<212> TYPE: PRT
<213> ORGANISM: Artificial Sequence
<220> FEATURE:
<223> OTHER INFORMATION: Humanized antibody

<400> SEQUENCE: 13

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asp Ser
                 20                  25                  30

Leu Ile Trp Leu Gln Gln Lys Pro Gly Lys Ala Pro Lys Arg Leu Ile
            35                  40                  45

Tyr Ala Thr Ser Ser Leu Asp Ser Gly Val Pro Ser Arg Phe Ser Gly
 50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Ser Gly Tyr Pro Leu
                 85                  90                  95

Thr Phe Gly Gln Gly Thr Lys Val Glu Ile Lys
                100                 105

<210> SEQ ID NO 14
```

```
<211> LENGTH: 36
<212> TYPE: PRT
<213> ORGANISM: Homo sapiens

<400> SEQUENCE: 14

Ser Asp Asp Gly Arg Lys Val Pro Val Gln Ala Tyr Ala Phe Gly
1               5                   10                  15

Lys Tyr Leu Gly Tyr Leu Lys Ile Glu Phe Asp Glu Arg Gly Asn Val
            20                  25                  30

Ile Ser Ser His
        35

<210> SEQ ID NO 15
<211> LENGTH: 10
<212> TYPE: PRT
<213> ORGANISM: Artificial Sequence
<220> FEATURE:
<223> OTHER INFORMATION: HCDR1

<400> SEQUENCE: 15

Gly Tyr Val Phe Ser Ser Tyr Thr Ile Asn
1               5                   10

<210> SEQ ID NO 16
<211> LENGTH: 17
<212> TYPE: PRT
<213> ORGANISM: Artificial Sequence
<220> FEATURE:
<223> OTHER INFORMATION: HCDR2

<400> SEQUENCE: 16

Ser Ile Tyr Pro Gly Asp Gly Asn Thr Asn Tyr Asn Arg Asn Phe Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: HCDR2

<400> SEQUENCE: 17

Arg Ile Tyr Pro Gly Asp Gly Asn Thr Asn Tyr Asn Arg Asn Phe Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: HCDR2

<400> SEQUENCE: 18

Thr Ile Tyr Pro Gly Asp Gly Asn Thr Asn Tyr Asn Arg Asn Phe Lys
1               5                   10                  15

Gly

<210> SEQ ID NO 19
<211> LENGTH: 17
<212> TYPE: PRT
<213> ORGANISM: Artificial Sequence
<220> FEATURE:
```

```
<223> OTHER INFORMATION: HCDR2

<400> SEQUENCE: 19

His Ile Tyr Pro Gly Asp Gly Asn Thr Asn Tyr Asn Arg Asn Phe Lys
1               5                   10                  15
Gly

<210> SEQ ID NO 20
<211> LENGTH: 3
<212> TYPE: PRT
<213> ORGANISM: Artificial Sequence
<220> FEATURE:
<223> OTHER INFORMATION: HCDR3

<400> SEQUENCE: 20

Leu Ala Asp
1

<210> SEQ ID NO 21
<211> LENGTH: 3
<212> TYPE: PRT
<213> ORGANISM: Artificial Sequence
<220> FEATURE:
<223> OTHER INFORMATION: HCDR3

<400> SEQUENCE: 21

Tyr Ala Asp
1

<210> SEQ ID NO 22
<211> LENGTH: 3
<212> TYPE: PRT
<213> ORGANISM: Artificial Sequence
<220> FEATURE:
<223> OTHER INFORMATION: HCDR3

<400> SEQUENCE: 22

Ile Ala Asp
1

<210> SEQ ID NO 23
<211> LENGTH: 9
<212> TYPE: PRT
<213> ORGANISM: Artificial Sequence
<220> FEATURE:
<223> OTHER INFORMATION: LCDR3

<400> SEQUENCE: 23

Gln Gln Tyr Ser Gly Tyr Pro Met Thr
1               5

<210> SEQ ID NO 24
<211> LENGTH: 9
<212> TYPE: PRT
<213> ORGANISM: Artificial Sequence
<220> FEATURE:
<223> OTHER INFORMATION: LCDR3

<400> SEQUENCE: 24

Gln Gln Tyr Ser Gly Tyr Pro Gly Thr
1               5

<210> SEQ ID NO 25
<211> LENGTH: 9
<212> TYPE: PRT
<213> ORGANISM: Artificial Sequence
```

```
<220> FEATURE:
<223> OTHER INFORMATION: LCDR3

<400> SEQUENCE: 25

Gln Gln Tyr Ser Gly Tyr Pro His Thr
1               5

<210> SEQ ID NO 26
<211> LENGTH: 9
<212> TYPE: PRT
<213> ORGANISM: Artificial Sequence
<220> FEATURE:
<223> OTHER INFORMATION: LCDR3

<400> SEQUENCE: 26

Gln Gln Thr Ser Gly Tyr Pro Arg Thr
1               5

<210> SEQ ID NO 27
<211> LENGTH: 9
<212> TYPE: PRT
<213> ORGANISM: Artificial Sequence
<220> FEATURE:
<223> OTHER INFORMATION: LCDR3

<400> SEQUENCE: 27

Gln Gln Tyr Ser Gly Tyr Pro Gln Thr
1               5

<210> SEQ ID NO 28
<211> LENGTH: 9
<212> TYPE: PRT
<213> ORGANISM: Artificial Sequence
<220> FEATURE:
<223> OTHER INFORMATION: LCDR3

<400> SEQUENCE: 28

Gln Gln Tyr Ser Gly Tyr Pro Ile Thr
1               5

<210> SEQ ID NO 29
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 29

Gln Val Lys Leu Gln Gln Ser Gly Ala Glu Leu Val Lys Pro Gly Ala
1               5                   10                  15

Ser Val Lys Ile Ser Cys Lys Ala Ser Gly Tyr Val Phe Ser Ser Tyr
            20                  25                  30

Trp Ile Asn Trp Val Lys Gln Arg Pro Gly Lys Gly Leu Glu Trp Ile
        35                  40                  45

Gly Gln Ile Tyr Pro Gly Asp Gly Asn Thr Asn Tyr Asn Arg Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Gly Leu Ala Asp Trp Gly Gln Gly Thr Thr Val Thr Val Ser Ser
            100                 105                 110
```

<210> SEQ ID NO 30
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 30

Gln Val Lys Leu Gln Gln Ser Gly Ala Glu Leu Val Lys Pro Gly Ala
1               5                   10                  15

Ser Val Lys Ile Ser Cys Lys Ala Ser Gly Tyr Val Phe Ser Ser Tyr
            20                  25                  30

Trp Ile Asn Trp Val Lys Gln Arg Pro Gly Lys Gly Leu Glu Trp Ile
        35                  40                  45

Gly Ser Ile Tyr Pro Gly Asp Gly Asn Thr Asn Tyr Asn Arg Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Gly Phe Ala Asp Trp Gly Gln Gly Thr Thr Val Thr Val Ser Ser
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 31

Gln Val Lys Leu Gln Gln Ser Gly Ala Glu Leu Val Lys Pro Gly Ala
1               5                   10                  15

Ser Val Lys Ile Ser Cys Lys Ala Ser Gly Tyr Val Phe Ser Ser Tyr
            20                  25                  30

Trp Ile Asn Trp Val Lys Gln Arg Pro Gly Lys Gly Leu Glu Trp Ile
        35                  40                  45

Gly Arg Ile Tyr Pro Gly Asp Gly Asn Thr Asn Tyr Asn Arg Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Gly Tyr Ala Asp Trp Gly Gln Gly Thr Thr Val Thr Val Ser Ser
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 32

Gln Val Lys Leu Gln Gln Ser Gly Ala Glu Leu Val Lys Pro Gly Ala
1               5                   10                  15

Ser Val Lys Ile Ser Cys Lys Ala Ser Gly Tyr Val Phe Ser Ser Tyr
            20                  25                  30

Trp Ile Asn Trp Val Lys Gln Arg Pro Gly Lys Gly Leu Glu Trp Ile
        35                  40                  45

```
Gly Gln Ile Tyr Pro Gly Asp Gly Asn Thr Asn Tyr Asn Arg Asn Phe
            50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Gly Ile Ala Asp Trp Gly Gln Gly Thr Thr Val Thr Val Ser Ser
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Val Phe Ser Ser Tyr
                20                  25                  30

Trp Ile Asn Trp Val Arg Gln Ala Pro Gly Gln Gly Leu Glu Trp Met
            35                  40                  45

Gly Thr Ile Tyr Pro Gly Asp Gly Asn Thr Asn Tyr Asn Arg Asn Phe
        50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Gly Phe Ala Asp Trp Gly Gln Gly Thr Leu Val Thr Val Ser Ser
            100                 105                 110
```

<210> SEQ ID NO 34
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 34

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Val Phe Ser Ser Tyr
                20                  25                  30

Trp Ile Asn Trp Val Arg Gln Ala Pro Gly Gln Gly Leu Glu Trp Met
            35                  40                  45

Gly His Ile Tyr Pro Gly Asp Gly Asn Thr Asn Tyr Asn Arg Asn Phe
        50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Gly Tyr Ala Asp Trp Gly Gln Gly Thr Leu Val Thr Val Ser Ser
            100                 105                 110
```

<210> SEQ ID NO 35
<211> LENGTH: 112
<212> TYPE: PRT

```
<213> ORGANISM: Artificial Sequence
<220> FEATURE:
<223> OTHER INFORMATION: Heavy chain variable domain

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Ser Tyr
            20                  25                  30

Thr Ile Asn Trp Val Arg Gln Ala Pro Gly Gln Gly Leu Glu Trp Met
        35                  40                  45

Gly Arg Ile Tyr Pro Gly Asp Gly Asn Thr Asn Tyr Asn Arg Asn Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Phe Ala Asp Trp Gly Gln Gly Thr Leu Val Thr Val Ser Ser
            100                 105                 110

<210> SEQ ID NO 36
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Ser Tyr
            20                  25                  30

Trp Ile Asn Trp Val Arg Gln Ala Pro Gly Gln Gly Leu Glu Trp Met
        35                  40                  45

Gly Arg Ile Tyr Pro Gly Asp Gly Asn Thr Asn Tyr Asn Arg Asn Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Phe Ala Asp Trp Gly Gln Gly Thr Leu Val Thr Val Ser Ser
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Ser Tyr
            20                  25                  30

Trp Ile Asn Trp Val Arg Gln Ala Pro Gly Gln Gly Leu Glu Trp Met
        35                  40                  45

Gly His Ile Tyr Pro Gly Asp Gly Asn Thr Asn Tyr Asn Arg Asn Phe
50                  55                  60
```

```
Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Phe Ala Asp Trp Gly Gln Gly Thr Leu Val Thr Val Ser Ser
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: Heavy chain variable domain

<400> SEQUENCE: 38

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Val Phe Ser Ser Tyr
                 20                  25                  30

Trp Ile Asn Trp Val Arg Gln Ala Pro Gly Gln Gly Leu Glu Trp Met
             35                  40                  45

Gly Arg Ile Tyr Pro Gly Asp Gly Asn Thr Asn Tyr Asn Arg Asn Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Leu Ala Asp Trp Gly Gln Gly Thr Leu Val Thr Val Ser Ser
            100                 105                 110
```

<210> SEQ ID NO 39
<211> LENGTH: 107
<212> TYPE: PRT
<213> ORGANISM: Artificial Sequence
<220> FEATURE:
<223> OTHER INFORMATION: Light chain variable domain

<400> SEQUENCE: 39

```
Asp Ile Glu Leu Thr Gln Ser Pro Ser Ser Leu Ser Ala Ser Leu Gly
 1               5                  10                  15

Glu Arg Val Ser Leu Thr Cys Arg Ala Ser Gln Asp Ile Gly Asp Ser
                 20                  25                  30

Leu Ile Trp Leu Gln Gln Glu Pro Asp Gly Thr Ile Lys Arg Leu Ile
             35                  40                  45

Tyr Ala Thr Ser Ser Leu Asp Ser Gly Val Pro Lys Arg Phe Ser Gly
 50                  55                  60

Ser Arg Ser Gly Thr Ser Tyr Ser Leu Thr Ile Ser Ser Val Glu Ala
 65                  70                  75                  80

Glu Asp Ala Ala Thr Tyr Tyr Cys Gln Gln Tyr Ser Gly Tyr Pro Met
                 85                  90                  95

Thr Phe Gly Ser Gly Thr Lys Leu Glu Ile Lys
            100                 105
```

<210> SEQ ID NO 40
<211> LENGTH: 107
<212> TYPE: PRT
<213> ORGANISM: Artificial Sequence
<220> FEATURE:
<223> OTHER INFORMATION: Light chain variable domain

<400> SEQUENCE: 40

Asp Ile Glu Leu Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asp Ser
            20                  25                  30

Leu Ile Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Thr Ser Tyr Ser Leu Thr Ile Ser Ser Val Glu Ala
65                  70                  75                  80

Glu Asp Ala Ala Thr Tyr Tyr Cys Gln Gln Tyr Ser Gly Tyr Pro Gly
                85                  90                  95

Thr Phe Gly Ser Gly Thr Lys Leu Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Light chain variable domain

<400> SEQUENCE: 41

Asp Ile Glu Leu Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asp Ser
            20                  25                  30

Leu Ile Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Thr Ser Tyr Ser Leu Thr Ile Ser Ser Val Glu Ala
65                  70                  75                  80

Glu Asp Ala Ala Thr Tyr Tyr Cys Gln Gln Tyr Ser Gly Tyr Pro His
                85                  90                  95

Thr Phe Gly Ser Gly Thr Lys Leu Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Light chain variable domain

<400> SEQUENCE: 42

Asp Ile Glu Leu Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asp Ser
            20                  25                  30

Leu Ile Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Thr Ser Tyr Ser Leu Thr Ile Ser Ser Val Glu Ala
65                  70                  75                  80

```
Glu Asp Ala Ala Thr Tyr Tyr Cys Gln Gln Tyr Ser Gly Tyr Pro Arg
                85                  90                  95

Thr Phe Gly Ser Gly Thr Lys Leu Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: Light chain variable domain

<400> SEQUENCE: 43

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Asp Ser
            20                  25                  30

Leu Ile Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
50                  55                  60

Ser Arg Ser Gly Thr Asp Tyr Thr Leu Thr Ile Ser Ser Val Gln Pro
65                  70                  75                  80

Glu Asp Phe Ala Thr Tyr Tyr Cys Gln Gln Tyr Ser Gly Tyr Pro Gln
                85                  90                  95

Thr Phe Gly Gln Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Light chain variable domain

<400> SEQUENCE: 44

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Asp Ser
            20                  25                  30

Leu Ile Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
50                  55                  60

Ser Arg Ser Gly Thr Asp Tyr Thr Leu Thr Ile Ser Ser Val Gln Pro
65                  70                  75                  80

Glu Asp Phe Ala Thr Tyr Tyr Cys Gln Gln Tyr Ser Gly Tyr Pro Ile
                85                  90                  95

Thr Phe Gly Gln Gly Thr Lys Val Glu Ile Lys
            100                 105
```